US012746313B2

(12) United States Patent
Thirumattathil Ashokan et al.

(10) Patent No.: US 12,746,313 B2
(45) Date of Patent: Sep. 29, 2026

(54) PERITONEAL DIALYSIS CYCLER USING MICROPUMP

(71) Applicants: Vantive US Healthcare LLC, Deerfield, IL (US); Vantive Health GMBH, Glattpark (CH)

(72) Inventors: Anoop Thirumattathil Ashokan, Bangalore (IN); Karthik Pitchaimani, Bangalore (IN); Sadashiva Kamath, Bangalore (IN); Sankar Murmu, Bangalore (IN); Emmanuel Thomas Nishanth Irudhayaraj, Bangalore (IN); Marcello Malagoli, Medolla (IT)

(73) Assignees: Vantive Healthcare US LLC, Deerfield, IL (US); Vantive Health GmbH, Glattpark (CH)

( * ) Notice: Subject to any disclaimer, the term of this patent is extended or adjusted under 35 U.S.C. 154(b) by 694 days.

(21) Appl. No.: 18/019,444

(22) PCT Filed: Jul. 29, 2021

(86) PCT No.: PCT/US2021/043614

§ 371 (c)(1),
(2) Date: Feb. 2, 2023

(87) PCT Pub. No.: WO2022/031504

PCT Pub. Date: Feb. 10, 2022

(65) Prior Publication Data

US 2023/0293797 A1 Sep. 21, 2023

(30) Foreign Application Priority Data

Aug. 3, 2020 (IN) ............................ 202041033187

(51) Int. Cl.
*A61M 1/28* (2006.01)
*A61M 1/14* (2006.01)

(52) U.S. Cl.
CPC .......... *A61M 1/281* (2014.02); *A61M 1/1524* (2022.05); *A61M 1/153* (2022.05);
(Continued)

(58) Field of Classification Search
CPC .... A61M 1/1524; A61M 1/153; A61M 1/154; A61M 1/155; A61M 1/156;
(Continued)

(56) References Cited

U.S. PATENT DOCUMENTS 10,087,931 B2 10/2018 Hayes-Pankhurst
2006/0189923 A1 8/2006 Neftel et al.
(Continued)

FOREIGN PATENT DOCUMENTS

EP 0772470 B1 8/2003

OTHER PUBLICATIONS

International Search Report from corresponding International Patent Application No. PCT/US2021/043614, mailed Dec. 2, 2021.
(Continued)

*Primary Examiner* — John Kim
(74) *Attorney, Agent, or Firm* — K&L Gates LLP

(57) ABSTRACT

A peritoneal dialysis ("PD") system includes a cycler having a micropump actuator, a pressure transducer, and at least one valve actuator; a disposable set including a micropump head sized and shaped for mating with and being driven by the micropump actuator, a pressure sensor configured to operably communicate with the pressure transducer, and at least one fluid valve portion or a portion of at least one fluid line for interfacing with the at least one valve actuator; and a control unit, wherein the disposable set may be arranged to allow, and the control unit may be programmed to operate the micropump actuator and the at least one valve actuator, so that fresh and used dialysis fluid flows through the micropump head in a same direction. The system may also
(Continued)

dampen pressure fluctuations via pressure pods, and may analyze the outputs from the pressure pods for patient empty and occlusion detection.

11 Claims, 13 Drawing Sheets

(52) U.S. Cl.
CPC ............ *A61M 1/154* (2022.05); *A61M 1/155* (2022.05); *A61M 1/156* (2022.05); *A61M 1/1562* (2022.05); *A61M 1/1565* (2022.05); *A61M 1/159* (2022.05); *A61M 1/28* (2013.01); *A61M 1/282* (2014.02); *A61M 2205/127* (2013.01); *A61M 2205/128* (2013.01); *A61M 2205/3331* (2013.01); *A61M 2205/3334* (2013.01); *A61M 2205/3341* (2013.01); *A61M 2209/088* (2013.01)

(58) Field of Classification Search
CPC .. A61M 1/1562; A61M 1/1565; A61M 1/159; A61M 1/28; A61M 1/281; A61M 1/282; A61M 2205/127; A61M 2205/128; A61M 2205/3331; A61M 2205/3334; A61M 2205/3341; A61M 2209/088
See application file for complete search history.

(56) References Cited

U.S. PATENT DOCUMENTS

| | | | |
|---|---|---|---|
| 2011/0160649 A1 | 6/2011 | Pan | |
| 2015/0014721 A1 | 1/2015 | Liao et al. | |
| 2017/0340794 A1 | 11/2017 | Hahne et al. | |
| 2019/0224400 A1 | 7/2019 | Wuppuluru | |
| 2019/0321535 A1 | 10/2019 | Beavers et al. | |

OTHER PUBLICATIONS

Written Opinion from corresponding International Patent Application No. PCT/US2021/043614, mailed Dec. 2, 2021.
International Preliminary Report on Patentability, PCT/US2021/043614 mailed Nov. 10, 2022—19 pages.

PERITONEAL DIALYSIS CYCLER USING MICROPUMP

PRIORITY CLAIM

This application is a national phase entry of PCT/US2021/043614, filed on Jul. 29, 2021, which claims priority to Indian Provisional Application No. 202041033187, filed on Aug. 3, 2020, the entire disclosures of which are incorporated by reference herein.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Known APD systems include a machine or cycler that accepts and actuates a pumping cassette having a hard part and a soft part that is deformable for performing pumping and valving operations. Sealing the fluid disposable cassette with a pneumatic path via a gasket to provide actuation has proven to be a potential field issue, which can delay treatment start time and affect use experience. Pneumatic cassette systems also produce acoustic noise, which may be a source of customer dissatisfaction.

For each of the above reasons, an improved APD machine is needed accordingly.

SUMMARY

The present disclosure sets forth a streamlined automated peritoneal dialysis APD cycler and associated system that uses a micropump. The micropumps of the cyclers of the present disclosure may be made of stainless steel and/or lower cost polymers. In one implementation, the pump head that contacts the dialysis fluid is disposable and is made of plastic. The lower actuator part of the micropump that drives the pump head in a cyclical manner and is reusable and is made of metal or plastic. The pump heads have an internal mechanism that drives the fluid, such as a rotating rotor, vane, a cam driven piston, or a flexing diaphragm. Each of the possible internal pumping head mechanisms is driven by the lower, e.g., reusable part of the micropump.

In one embodiment, volumetric accuracy is derived from the pump itself. That is, each rotation of the rotor or vane, or each actuation of a piston or diaphragm, pumps a known quantity of fluid, so that the total volume of dialysis fluid pumped to or removed from the patient is the volume per stroke multiplied by the number of strokes. Certain rotating vane pumps suitable for the micropump APD cycler and associated system of the present disclosure are only accurate in one dimension.

Fresh dialysis fluid pumped by the micropump is heated in one embodiment via an inline heater, which may be a resistance plate heater, such as a clamshell heater into which a serpentine fluid pathway of the disposable set is placed. Other types of inline heating may be used alternatively or additionally, such as radiant heating or inductive heating. Batch heaters may further alternatively be employed.

The valves used with the micropump APD cycler in one embodiment are two- or three-way stopcock valves having a disposable portion that includes a stem that is rotated into multiple positions to direct fluid in a desired direction. The disposable stem fits onto a reusable actuator that rotates the stem to a desired position. In an alternative embodiment, electromechanical pinch valves may be used to occlude the lines leading to the micropump and pressure sensors. In a further alternative embodiment, cassette-based valves, such as pneumatic valves may be used.

The rotating positive displacement micropumps of the present disclosure, such as rotating rotor or vane pumps, produce pulsating inlet and outlet pressures in one embodiment, which may be uncomfortable to the patient. It is accordingly contemplated to place a pressure sensor, such as a pod pressure sensor, between the micropump and the patient to measure the positive pressure of fresh dialysis fluid pumped to the patient and the negative pressure of used dialysis fluid removed from the patient. The pod pressure sensor includes a pod having a flexible membrane or diaphragm that separates a dialysis fluid side of the pod from a pressure transmission fluid (e.g., air) side of the membrane. The membrane or diaphragm also serves a second purpose, namely, to dampen the pump's input and output pressure fluctuations.

A second pressure sensor or pod may be placed between the micropump and the fluid source or drain. The fluid source may be multiple bags of premixed dialysis fluid or an online fluid source that mixes dialysis fluid at the point of use.

Another solution contemplated for the system and methodology of the present disclosure for managing the pulsatile nature of the micropump is to employ flowrate profiles. The peritoneal dialysis treatment of the present disclosure includes the cyclical introduction and removal of dialysis fluid to and from the patient's peritoneal cavity. Excess pressure in either direction may cause patient discomfort. The present system and associated methodology however capitalize on the phenomenon that the patient is most susceptible to discomfort at the beginning and end of both patient fills and patient drains. During the middle of both the fills and drains, patient discomfort is less likely and/or less intense. It is accordingly contemplated to employ flowrate profiles that begin a patient fill or drain at a lower flowrate, which is maintained until a certain amount of fluid is delivered to or removed from the patient, e.g., the first ten percent of a total fill or drain volume, after which the flowrate is ramped up to full speed according to a desired acceleration curve, e.g., linear or sinusoidal. At a certain point near the end of the fill or drain, e.g., the last ten percent, the flowrate is ramped down to the lower flowrate according to a desired deceleration curve, e.g., linear or sinusoidal. The system and methodology of the present disclosure may employ the flowrate profiles alone or in combination with pressure dampeners or pod pressure sensors to address the pulsatile input and output of the micropumps.

The amount of used dialysis fluid or effluent that needs to be removed from the patient after a dwell period is not known exactly because it is not known how much ultrafiltration (patient water) has osmosed into the patient's peritoneal cavity during a subsequent dwell phase, and it is not known how much residual fluid remains in the patient's cavity prior to the previous patient fill. The micropump system and method are accordingly able to detect when the patient is empty or near empty in one embodiment, so that a patient drain via the micropump can be terminated. In one embodiment, the output of pressure sensor located between the patient and the micropump is monitored. If a negative inlet pressure to the micropump increases (becomes more negative), e.g., to a threshold negative pressure or at a threshold rate of change in pressure, the control unit of the micropump APD cycler determines that the patient is empty or near empty. The negative pressure increases when the patient reaches empty because the pores in the patient's indwelling catheter begin to become blocked and a higher pressure gradient is needed to maintain flow. When the negative pressure spike is detected, the control unit of the micropump APD cycler causes the micropump to stop, completing the drain. The cycler then transitions to fill the patient with new dialysis fluid.

Peritoneal dialysis is commonly performed while the patient is sleeping, during which the patient may shift or turn and consequently fold or kink the patient line, occluding flow. The micropump system and method of the present disclosure is accordingly configured to use the pressure sensor or pod located between the micropump and the patient to look for a rise in pressure (an increase in negative pressure for a drain and an increase in positive pressure for a fill). If the pressure rises to a certain point, or a certain rate of pressure increase is detected, the patient fill or drain is stopped, and an alarm is sounded.

In light of the disclosure set forth herein, and without limiting the disclosure in any way, in a first aspect of the present disclosure, which may be combined with any of other aspect discussed herein, a peritoneal dialysis ("PD") system includes: a cycler including a micropump actuator, a pressure transducer, and at least one valve actuator; a disposable set including a micropump head sized and shaped for mating with and being cyclically driven by the micropump actuator, a pressure sensor configured to operably communicate with the pressure transducer, and at least one fluid valve portion or a portion of at least one fluid line for interfacing with the at least one valve actuator; and a control unit, wherein the disposable set is arranged to allow, and the control unit is programmed to operate the micropump actuator and the at least one valve actuator so that fresh and used dialysis fluid flows through the micropump head in a same direction.

In a second aspect of the present disclosure, which may be combined with any of other aspect discussed herein, the micropump actuator and the micropump head are more accurate in the same direction than in a reverse direction.

In a third aspect of the present disclosure, which may be combined with any of other aspect discussed herein, the micropump actuator includes a keyed driver and the micropump head includes a keyed recess sized and shaped for mating with the keyed driver of the micropump actuator.

In a fourth aspect of the present disclosure, which may be combined with any of other aspect discussed herein, the pressure sensor includes a fluid pressure chamber having a sealed diaphragm configured to fluctuate due to pressure variations, and wherein the cycler includes a transmission fluid chamber positioned and arranged to mate with the fluid pressure chamber when the disposable set is mounted to the cycler.

In a fifth aspect of the present disclosure, which may be combined with any of other aspect discussed herein, a transmission fluid line extends from the transmission fluid chamber to the pressure transducer.

In a sixth aspect of the present disclosure, which may be combined with any of other aspect discussed herein, the pressure sensor includes a fluid pressure chamber having a sealed diaphragm configured to fluctuate due to pressure variations, and a transmission fluid chamber sealed to the fluid pressure chamber.

In a seventh aspect of the present disclosure, which may be combined with any of other aspect discussed herein, the pressure sensor interfaces with the pressure transducer via a transmission fluid line placed in fluid communication with the transmission fluid chamber.

In an eighth aspect of the present disclosure, which may be combined with any of other aspect discussed herein, at least one fluid valve portion includes a rotating stem and the at least one valve actuator is configured to rotate the rotating stem.

In a ninth aspect of the present disclosure, which may be combined with any of other aspect discussed herein, at least one valve actuator is a pinch valve positioned and arranged to occlude the portion of at least one fluid line when the disposable set is mounted to the cycler.

In a tenth aspect of the present disclosure, which may be combined with any of other aspect discussed herein, the disposable set includes an inline fluid heating pathway or a batch heater container, and the cycler includes an inline fluid heater or batch fluid heater positioned and arranged to heat the inline fluid heating pathway or the batch heater container, respectively, when the disposable set is mounted to the cycler.

In an eleventh aspect of the present disclosure, which may be combined with any of other aspect discussed herein, the disposable set being arranged to allow fresh and used dialysis fluid to flow through the micropump head in a same direction includes disposing both a patient line and a drain line of the disposable set, at least during a patient fill phase, downstream of the micropump head.

In a twelfth aspect of the present disclosure, which may be combined with any of other aspect discussed herein, a peritoneal dialysis ("PD") system includes: a cycler including a micropump actuator, and at least one valve actuator; a disposable set including a micropump head sized and shaped for mating with and being cyclically driven by the micropump actuator, and at least one fluid valve portion or a portion of at least one fluid line for interfacing with the at least one valve actuator; and a control unit programmed to operate the micropump actuator so that at least one of fresh or used dialysis fluid flows at a lower flowrate at a beginning of at least one of a patient fill or a patient drain, respectively, than during a middle portion of the at least one of the patient fill or the patient drain.

In a thirteenth aspect of the present disclosure, which may be combined with any of other aspect discussed herein, the control unit is further programmed to operate the micropump actuator so that the at least one of fresh or used dialysis fluid flows at a lower flowrate at an end of the at least one of the patient fill or the patient drain, respectively, than during a middle portion of the at least one of the patient fill or the patient drain.

In a fourteenth aspect of the present disclosure, which may be combined with any of other aspect discussed herein, the disposable set further includes at least one pressure sensor positioned and arranged to dampen pressure fluctuations of fresh or used dialysis fluid flowing between the micropump head and a patient line.

In a fifteenth aspect of the present disclosure, which may be combined with any of other aspect discussed herein, a peritoneal dialysis ("PD") system includes: a cycler including a micropump actuator, and a pressure transducer; a disposable set including a micropump head sized and shaped for mating with and being cyclically driven by the micropump actuator, and a pressure sensor configured to operably communicate with the pressure transducer; and a control unit programmed to monitor a negative pressure from the pressure transducer during a patient drain in which the micropump actuator actuates the micropump head to remove used dialysis fluid from a patient, and wherein if the sensed negative pressure increases to a predefined extent, the control unit ends the patient drain.

In a sixteenth aspect of the present disclosure, which may be combined with any of other aspect discussed herein, the predefined extent includes (i) a threshold value, (ii) a threshold rate of change of negative pressure, or (iii) a combination of (i) and (ii).

In a seventeenth aspect of the present disclosure, which may be combined with any of other aspect discussed herein, a peritoneal dialysis ("PD") system includes: a cycler including a micropump actuator, and a pressure transducer; a disposable set including a micropump head sized and shaped for mating with and being cyclically driven by the micropump actuator, and a pressure sensor configured to operably communicate with the pressure transducer; and a control unit programmed to monitor a negative pressure from the pressure transducer and a drain flowrate during a patient drain in which the micropump actuator actuates the micropump head to remove used dialysis fluid from a patient, and wherein if the sensed negative pressure increases to a first predefined extent and/or if the drain flowrate falls to a second predefined extent, the control unit determines that a drain occlusion has occurred.

In an eighteenth aspect of the present disclosure, which may be combined with any of other aspect discussed herein, the first predefined extent includes (i) a threshold value, (ii) a threshold rate of change of negative pressure, or (iii) a combination of (i) and (ii).

In a nineteenth aspect of the present disclosure, which may be combined with any of other aspect discussed herein, the second predefined extent includes (i) a threshold value, (ii) a threshold rate of change of flowrate, (iii) a combination of (i) and (ii), or (iv) a combination of (i), (ii) or (iii) with an output from a flowrate sensor.

In a twentieth aspect of the present disclosure, which may be combined with any of other aspect discussed herein, the control unit upon determining that the drain occlusion has occurred causes an instruction to be provided for clearing the occlusion.

In a twenty-first aspect of the present disclosure, which may be combined with any of other aspect discussed herein, a peritoneal dialysis ("PD") system includes: a cycler including a micropump actuator, and a pressure transducer; a disposable set including a micropump head sized and shaped for mating with and being cyclically driven by the micropump actuator, and a pressure sensor configured to operably communicate with the pressure transducer; and a control unit programmed to monitor a positive pressure from the pressure transducer and a fill flowrate during a patient fill in which the micropump actuator actuates the micropump head to deliver fresh dialysis fluid to a patient, and wherein if the sensed positive pressure increases to a first predefined extent and/or if the fill flowrate falls to a second predefined extent, the control unit determines that a fill occlusion has occurred.

In a twenty-second aspect of the present disclosure, which may be combined with any of other aspect discussed herein, the first predefined extent includes (i) a threshold value, (ii) a threshold rate of change of positive pressure, or (iii) a combination of (i) and (ii).

In a twenty-third aspect of the present disclosure, which may be combined with any of other aspect discussed herein, the second predefined extent includes (i) a threshold value, (ii) a threshold rate of change of flowrate, (iii) a combination of (i) and (ii), or (iv) a combination of (i), (ii) or (iii) with an output from a flowrate sensor.

In a twenty-fourth aspect of the present disclosure, which may be combined with any of other aspect discussed herein, the control unit upon determining that the fill occlusion has occurred causes an instruction to be provided for clearing the occlusion.

In a twenty-fifth aspect, any of the features, functionality and alternatives described in connection with any one or more of FIGS. 1 to 13B may be combined with any of the features, functionality and alternatives described in connection with any other of FIGS. 1 to 13B.

It is accordingly an advantage of the present disclosure to provide a micropump driven APD system, which is portable to ultra-portable (e.g., wearable) and compact.

It is another advantage of the present disclosure to provide a micropump driven APD system, wherein the micropump is at least partially reusable.

It is a further advantage of the present disclosure to provide a micropump driven APD system, which eliminates certain sealing issues present in known APD systems.

It is yet a further advantage of the present disclosure to provide a micropump driven APD system, which eliminates bulky pneumatic equipment associated with certain APD systems.

It is yet another advantage of the present disclosure to provide a micropump driven APD system, which manages peritoneal dialysis fluid flow so as to be within safe and comfortable patient pressure limits.

It is still another advantage of the present disclosure to provide a micropump driven APD system, which may reduce time to detect a patient empty condition and thus overall treatment time.

It is still a further advantage of the present disclosure to provide a micropump driven APD system, which may reduce patient exposure time to lower pressure.

Further still, it is an advantage of the present disclosure to provide a micropump driven APD system that can maintain flowrates under partial occlusion and thereby maintain or improve treatment time as compared with other APD systems.

Moreover, it is an advantage of the present disclosure to provide a portable APD system, wherein solution bag size may be reduced for treatment on the go.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
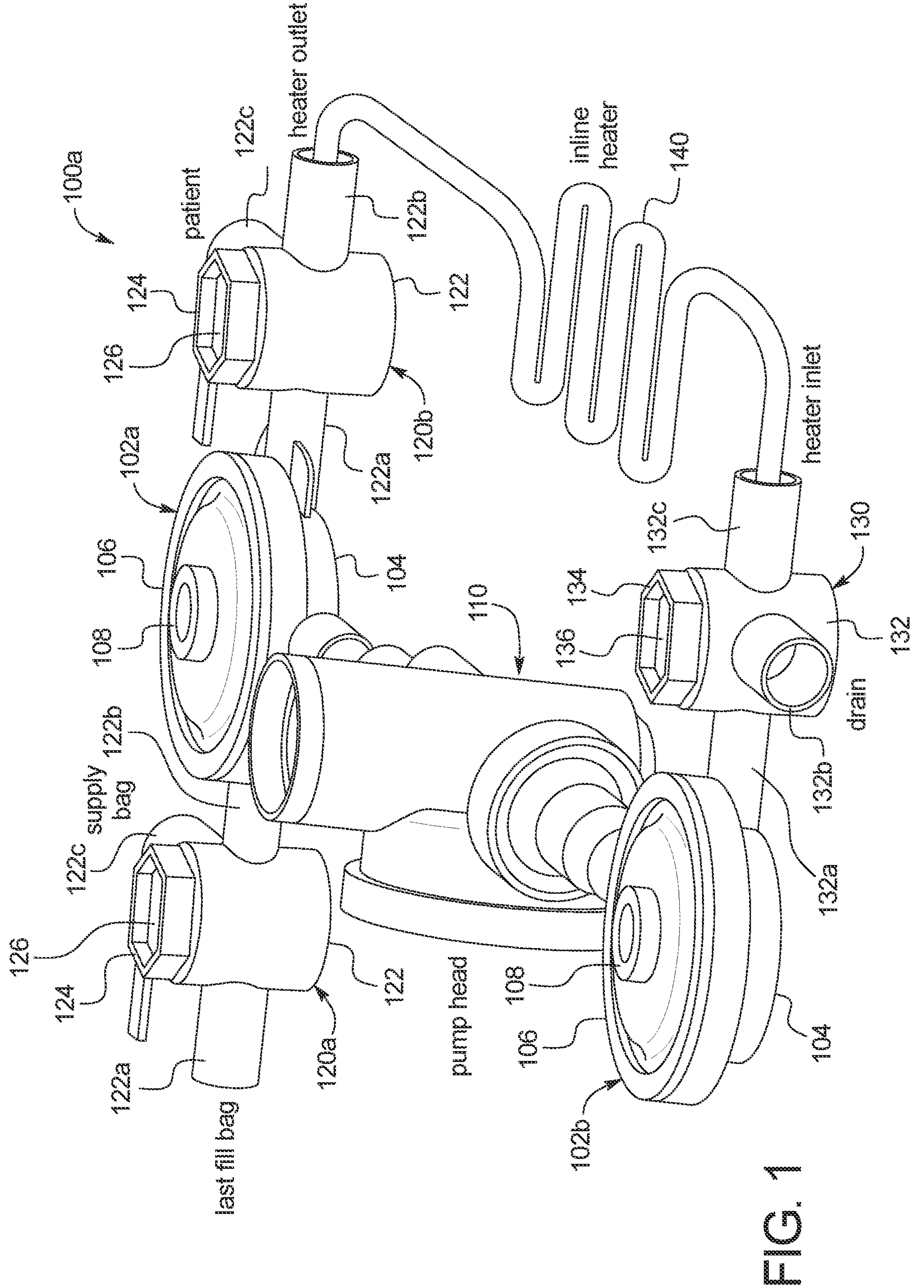
FIG. 1 is a perspective view from the bottom of one embodiment for a disposable set for the micropump automated peritoneal dialysis ("APD") cycler of the present disclosure, wherein the disposable set uses stopcock valves.

Referring now to the drawings and in particular to FIG. 1, a disposable set 100*a* having a disposable, fluid-contacting micropump head 110 is illustrated. Fluid-contacting micropump head 110 is located between first and second disposable, pressure sensors or pods 102*a* and 102*b*. Pressure sensor or pod 102*a* is located fluidly between first and second three-way disposable, fluid-contacting stopcock valve portions 120*a* and 120*b*. Pressure sensor 102*b* or pod is located fluidly between fluid-contacting micropump head 110 and a three-way disposable, fluid-contacting stopcock valve portion 130.

In the illustrated embodiment, disposable set 100*a* includes an inline fluid heating pathway 140. Inline fluid heating pathway 140 in the illustrated embodiment is located fluidly between first and second disposable, pressure sensors 102*a* and 102*b* and valve portions 120*b* and 130. Suitable materials for any of disposable set 100*a*, including any of pressure sensors 102*a* and 102*b*, fluid-contacting micropump head 110, fluid-contacting stopcock valve portions 120*a*, 120*b* and 130, inline fluid heating pathway 140 and any associated tubing include polyvinyl chloride ("PVC"), polyethylene ("PE"), polyurethane ("PU"), polycarbonate or other non-PVC material.

Figure 2:
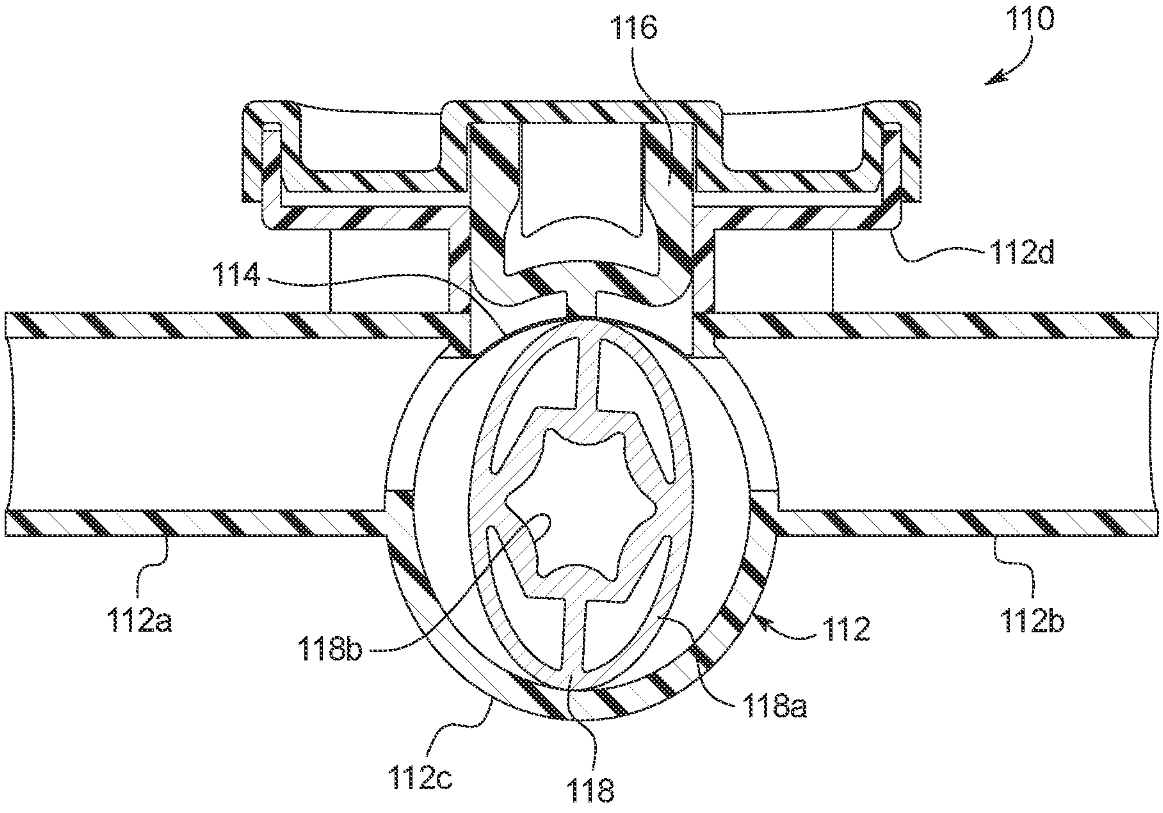
FIG. 2 is an enlarged view of one embodiment for a disposable, fluid-contacting micropump head of the present disclosure provided with the disposable set of FIG. 1.

Disposable set 100*a* is illustrated from the bottom to show how different disposable components interact with their corresponding actuators. The underside of fluid-contacting micropump head 110 is illustrated in more detail in connection with FIG. 2. The micropump including micropump head 110 may be provided for example by Quantex, London, W6 7HJ, UK. FIG. 2 illustrates that fluid-contacting micropump head 110 includes a housing 112 including or defining an inlet port 112*a*, an outlet port 112*b*, a rotor holding section 112*c* in fluid communication with the inlet port 112*a* and outlet port 112*b*, and a plunger holding section 112*d* that does not communicate fluidly with ports 112*a*, 112*b* or rotor holding section 112*c*. In an alternative embodiment, plunger holding section 112*d* may communicate fluidly with outlet port 112*b*. A thin membrane 114 separates rotor holding section 112*c* from membrane holding section 112*d*. A spring-loaded plunger 116 is fitted into membrane holding section 112*d* and applies a desired amount of holding force to membrane 114, which may be attached to housing 112 or be molded as a thin portion of housing 112, and therefore be of the same material as housing 112.

The holding force maintains membrane so as to be in contact with a rotor 118 over a full revolution and for each revolution. Rotor 118 includes an elliptical or oblong fluid contacting driver 118*a* that moves fresh or used dialysis fluid from inlet port 112*a* to outlet port 112*b*. Rotor 118 also includes or defines a keyed recess 118*b*, which in the illustrated embodiment has the shape of a star. Keyed recess 118*b* fits onto a reusable micropump actuator, which is located within a cycler or machine of the present disclosure. The micropump actuator is operated under control of a control unit to spin at a desired or preprogrammed rate. The rate is variable in certain embodiments for reasons discussed herein.

In an embodiment, fluid-contacting micropump head 110 may be operated in two directions, such that the roles of inlet port 112*a* and outlet port 112*b* may be reversed. Certain types of micropumps are only accurate in one direction, so that at least some of the flowpaths discussed below only route fresh or used dialysis fluid in one direction through micropump head 110, at least where accuracy is required. Regarding accuracy, in FIG. 2, fluid-contacting micropump head 110 is constructed such that one full rotation of rotor 118 pumps a known amount of fresh or used dialysis fluid. The control unit knows how many revolutions the micropump actuator makes over a fill or drain phase, for example, by providing a motor encoder with the motor of the micropump actuator, which outputs the number of revolutions and partial revolutions made to the control unit. The control unit then multiplies the number of full and partial revolutions by the known volume per revolution to determine the amount of fresh or used dialysis fluid delivered on a real time basis. Volumetric accuracy for fluid-contacting micropump head 110 of FIG. 2 has been demonstrated to be <±2% for a flowrate range of 35 mL/min to 350 mL/min. The number of full and partial revolutions divided by the time period over which the revolutions have occurred determines dialysis fluid flowrate, which the control unit controls, for example, by controlling the current provided to the motor of the micropump actuator. Example ranges for revolutions per second ("rps") for micropump head 110 to achieve the flowrate range of 35 mL/min to 350 mL/min are 1 rps to 10.4 rps.

Further information regarding the micropump of FIG. 2 may be found in U.S. Pat. No. 10,087,931, the entire contents of which are herein incorporated by reference and relied upon. The micropumps of the present disclosure are, however, not limited to the type illustrated in connection with FIG. 2. For example, the micropumps may instead be piston and cylinder pumps, e.g., a Swissinova Tpump or a Swissinova Nao Stedi pump described in U.S. Patent Publication No. 2015/00147210, the entire contents of which are herein incorporated by reference and relied upon. Such piston and cylinder pumps likewise have reusable and a disposable components and control volume accurately by enabling known volume pump strokes to be summed.

The micropump of FIG. 2 including fluid-contacting micropump head 110 is a relatively continuous pump because it pulls dialysis fluid on the suction side of housing 112 and rotor 118 as rotor 118 pushes dialysis fluid out of housing 112. Over a full stroke, however, fluid-contacting micropump head 110 is pulsatile as the per-stroke flowrate varies depending on the location fluid contacting driver 118*a* over a revolution. It is accordingly contemplated to place a pressure sensor 102*a* and 102*b* at least one of upstream and/or downstream of fluid-contacting micropump head 110. Pressure sensors 102*a* and 102*b* and their associated pressure transducers output to the control unit measure a positive (e.g., to the patient) or negative (e.g., from the patient) dialysis fluid pumping pressure. Pressure sensors or pods 102*a* and 102*b* in one embodiment each include a pressure transmitting diaphragm, which dampens pressure pulses and smoothens downstream fluid flow as illustrated below in connection with FIGS. 11A, 11B, 12A, 12B, 13A and 13B.

In particular, FIG. 1 illustrates that pressure sensors 102*a* and 102*b* each include a dialysis fluid pressure chamber 104 and a transmission fluid (e.g., air) chamber 106 that seal together about a pressure transmitting diaphragm (not seen in FIG. 1). Transmission fluid chamber 106 includes or defines a transmission line port 108 that accepts a transmission line (not illustrated), which extends to a pressure transducer located within the cycler of the present system and method. Positive or negative fluid pressure within dialysis fluid pressure chamber 104 is transmitted via the diaphragm to the transmission fluid or air within transmission fluid chamber 106 and the transmission line to pressure transducer, which outputs a corresponding pressure signal to the control unit of the APD cycler. In the illustrated embodiment of FIG. 1, dialysis fluid pressure chamber 104 and the pressure diaphragm are disposable, e.g., single use disposable. The pressure transmission line to pressure transducer is reusable. Transmission fluid chamber 106 may be reusable or disposable, that is, when installing disposable set 100*a* for operation with the cycler, either (i) dialysis fluid pressure chamber 104 becomes removably sealed to transmission fluid chamber 106 or (ii) the transmission fluid line becomes removably sealed to transmission line port 108 of transmission fluid chamber 106. In an alternative implementation of either (i) or (ii) above, the pressure transmission line is not provided and transmission fluid chamber 106 instead couples directly to the pressure transducer for operation.

FIG. 1 also illustrates that three-way fluid-contacting stopcock valve portions 120*a* and 120*b* each include a valve housing 122 and associated inlet and outlet ports 122*a*, 122*b* and 122*c*. A valve stem 124 is rotationally sealed within valve housing 122 and is configured to allow or disallow fresh or used dialysis fluid flow between inlet and outlet ports 122*a*, 122*b* and 122*c* through housing 122, depending on the rotational position of valve stem 124. Valve stem 124 in an embodiment includes an open and a closed position. Valve stem 124 includes or defines a keyed recess 126, which in the illustrated embodiment has the shape of a hexagon. Keyed recess 126 fits onto a reusable three-way valve actuator, which is located within the cycler or machine of the present disclosure. The three-way actuators associated with fluid-contacting stopcock valve portions 120*a* and 120*b* are operated under control of the control unit to rotate valve stem 124 to the open (allow flow) or closed (no flow) position.

FIG. 1 also illustrates that three-way fluid-contacting stopcock valve portion 130 includes a valve housing 132 and associated inlet and outlet ports 132*a*, 132*b* and 132*c*. A valve stem 134 is rotationally sealed within valve housing 132 and is configured to allow or disallow fresh or used dialysis fluid flow between (i) inlet and outlet ports 132*a* and 132*b*, (ii) inlet and outlet ports 132*a* and 132*c*, and (iii) inlet and outlet ports 132*b* and 132*c* (e.g., in case inline fluid heating pathway 140 needs to be drained), and (iv) total occlusion of flow through housing 132, depending on the rotational position of valve stem 134. Valve stem 134 in an embodiment includes two open positions and a closed position. Valve stem 134, like stem 124, includes or defines a keyed recess 136, which in the illustrated embodiment also has the shape of a hexagon. Keyed recess 136 fits onto a reusable three-way valve actuator, which is located within the cycler or machine of the present disclosure. The three-way actuator associated with fluid-contacting stopcock valve portions 130 is operated under control of the control unit to rotate valve stem 134 to (i) a first open position (allow between ports 132*a* and 132*b*), (i) a second open position (allow between ports 132*a* and 132*c*) or (iii) a closed (no flow) position. In general, any of the ports for each of three-way valves 120*a*, 120*b* and 130 can be fluidly communicated with any other of the three ports, e.g., during final emptying of disposable set 100*a* at the end of treatment.

In the illustrated embodiment, tubing attached to port 122*a* of three-way fluid-contacting stopcock valve portion 120*a* extends to a last fill container or bag, which may for example contain icodextrin, which has a different formulation than the peritoneal dialysis solution used in prior fills. Tubing attached to port 122*c* of three-way fluid-contacting stopcock valve portion 120*a* extends to a supply container or bag of peritoneal dialysis solution used in the prior fills. Tubing attached to port 122*c* of three-way fluid-contacting stopcock valve portion 120*b* extends to the patient. Tubing attached to port 122*b* of three-way fluid-contacting stopcock valve portion 120*b* extends to an inline heater outlet lines. Tubing attached to port 132*c* of three-way fluid-contacting stopcock valve portion 130 extends to the inline heater inlet line. Tubing attached to port 132*b* of three-way fluid-contacting stopcock valve portion 130*a* extends to a drain container or bag or to a house drain.

Figure 3:
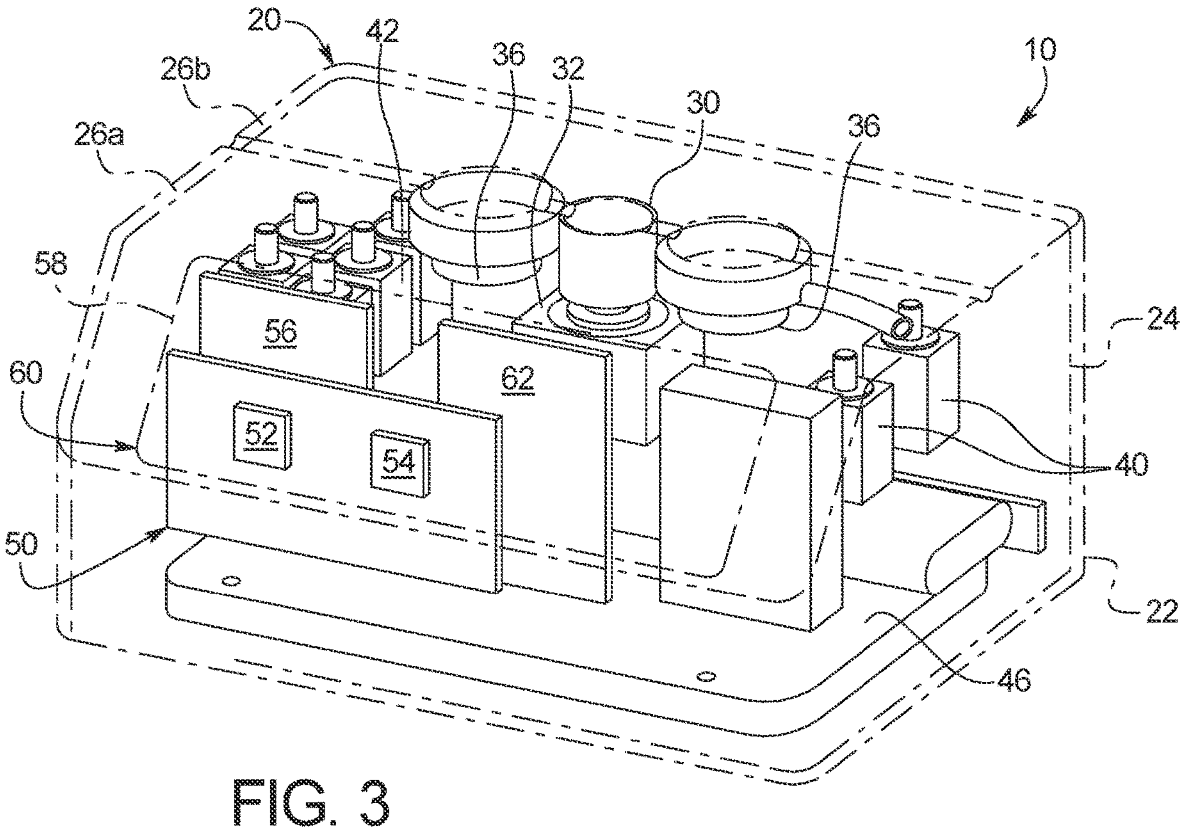
FIG. 3 is a perspective view of one embodiment of a micropump APD cycler of the present disclosure operating the disposable set of FIG. 1.

FIG. 3 illustrates one possible operational mounting arrangement for disposable set 100*a*. Here, system 10 includes an APD cycler or machine 20. APD cycler 20 includes a housing 22 having a base 24 and lids 26*a* and 26*b* hingedly connected to base. Housing 22 may be made of metal, such as stainless steel, steel, aluminum and combinations thereof and/or a plastic, such as, any one or more of polyvinyl chloride ("PVC"), polyethylene ("PE"), polyurethane ("PU"), or polycarbonate. Base houses a control unit 50, which includes one or more processor 52, one or more memory 54 and a video controller 56 for controlling a video monitor 58. Video monitor 58 is part of an overall user interface 60 for systems 10 described herein. User interface 60 includes any one or more of a touch screen overlay operable with video monitor 58 and/or one or more electromechanical input device, e.g., membrane switches, for inputting information into control unit. Video monitor 58 and speakers (e.g., operable with a sound card 62 of control unit 50) are provided to output information to the patient or user, e.g., alarms, alerts and/or voice guidance commands. Control unit 50 may also include a transceiver and a wired or wireless connection to a network, e.g., the internet, for sending treatment data to and receiving prescription instructions from a doctor's or clinician's server interfacing with a doctor's or clinician's computer.

Lids 26*a* and 26*b* open to allow disposable set 100*a* to be translated down into APD cycler 20 so that keyed recess 118*b* of rotor 118 of fluid-contacting micropump head 110 fits onto a mating keyed driver of reusable micropump actuator 30. Reusable micropump actuator 30 in the illustrated embodiment is driven by a motor 32 under control of control unit 50, such as a stepper motor, which may be fitted with an encoder that outputs to the control unit.

In FIG. 3 regarding pressure sensors or pods 102*a* and 102*b*, either (i) dialysis fluid pressure chamber 104 becomes removably sealed to transmission fluid chamber 106 located within cycler base 24 and reusable or (ii) the transmission fluid line located within cycler base 24 becomes removably sealed to transmission line port 108 of transmission fluid chamber 106 (here disposable). In an alternative implementation of either (i) or (ii) above, the pressure transmission line is not provided and transmission fluid chamber 106 instead couples directly to the pressure transducer 36 (located within cycler base 24) for operation. In an embodiment, a separate pressure transducer 36 outputting to control unit 50 is provided for each pressure sensor 102*a* and 102*b*

In FIG. 3, keyed recesses 126 of valve stems 124 of three-way fluid-contacting stopcock valve portions 120*a* and 120*b* fit onto a mating reusable three-way valve actuators 40 located within cycler base 24. Keyed recess 136 of valve stem 134 of three-way fluid-contacting stopcock valve portion 130 fits onto a mating reusable three-way valve actuator 42 located within cycler base 24. Valve actuators 40 and 42 are under the control of control unit 50 and operate as described above to selectively allow or disallow fresh or used dialysis fluid flow in desired directions.

In FIG. 3, inline fluid heating pathway 140 of FIG. 1 is located within an inline fluid heater 46 located with cycler base 24. Inline fluid heater 46 is under control of control unit 50 and may be a resistance plate heater, such as a clamshell heater into which a serpentine pathway, for example, of heating pathway 140 is placed. Other types of inline heating may be used alternatively or additionally, such as radiant heating and/or inductive heating. Heater 46 may further alternatively be a batch heater. Here, the heating portion of the disposable set is a bag or pouch that receives fresh dialysis fluid for heating. In FIG. 3, inline fluid heater 46 is located near the bottom of cycler base 24. In alternative embodiments, inline fluid heater 46 is located at the back or one of the sides of cycler base 24.

Figure 4:
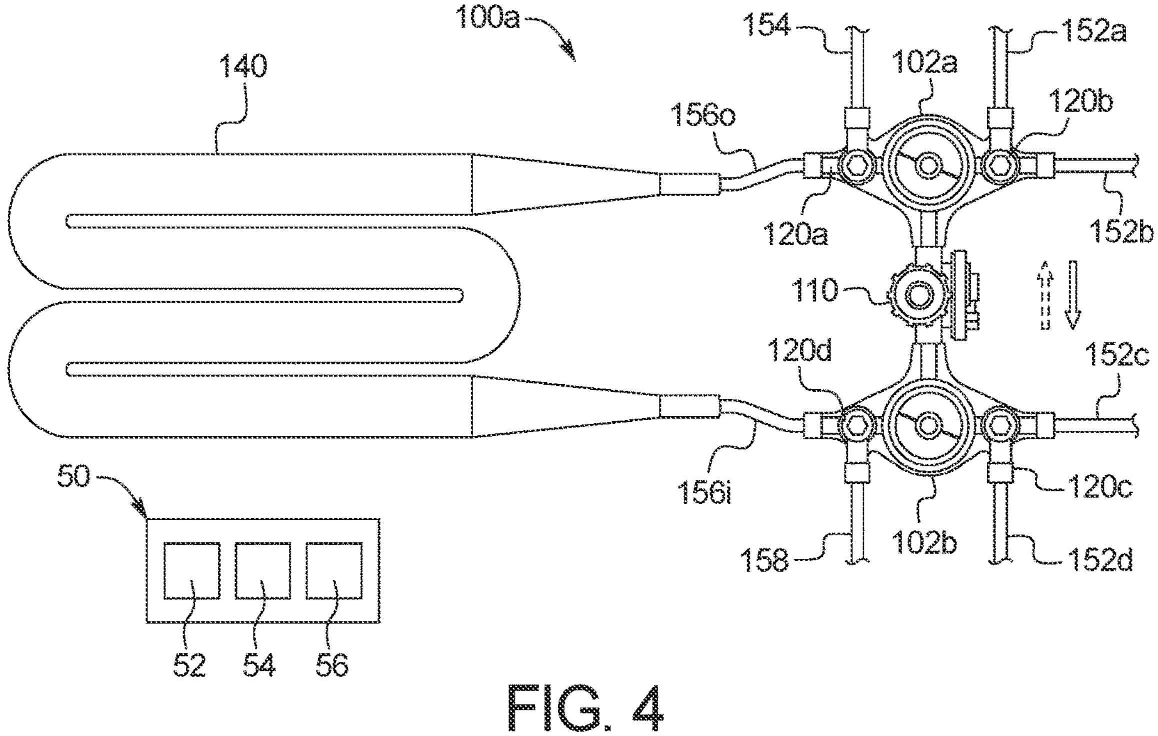
FIG. 4 is a plan view of another embodiment for a disposable set for the APD cycler of the present disclosure, wherein the disposable set is configured for operation with multiple three-way valves.

Referring now to FIG. 4, an alternative implementation of disposable set 100*a* is illustrated using four three-way disposable, fluid-contacting stopcock valve portions 120*a* to 120*d* instead of two three-way valve portions and a single three-way disposable, fluid-contacting stopcock valve portion 130. Fluid-contacting micropump head 110 is provided again with first and second disposable, pressure sensors 102*a* and 102*b*. In the illustrated embodiment, three-way fluid valve portions 120*b* and 120*c* are selectively fluidly connected to supply lines 152*a* to 152*c*, which are in turn connected to fresh dialysis fluid supply containers (e.g., bags) and a last fill line 152*d*, which is connected to a last fill dialysis fluid supply container (e.g., bag, last fill for extended dwell). Three-way fluid valve portion 120*a* is alternatively fluidly connected to a patient line 154 leading to the patient or a heater outlet line 156*o* leading to an exit of inline serpentine heating pathway 140. Three-way fluid valve portion 120*d* is alternatively fluidly connected to a drain line 158 leading to a drain container (e.g., bag) or house drain (e.g., toilet or bathtub) or a heater inlet line 156*i* leading to an inlet of inline serpentine heating pathway 140.

In FIG. 4, for a patient fill, fresh dialysis fluid flows from one of supply lines 152*a* to 152*c* or last fill line 152*d*, through inlet pressure sensor 102*a*, micropump head 110, outlet pressure sensor 102*b*, heater inlet line 156*i*, serpentine heating pathway 140, heater outlet line 156*o*, to patient line 154 and the patient. For upper supply lines 152*a* and 152*b*, micropump head 110 pushes fresh dialysis fluid through serpentine heating pathway 140 to the patient via patient line 154.

For lower supply and last fill lines 152*c* and 152*d*, micropump head 110 is run in reverse to pull fresh dialysis fluid from a supply container connected to lines 152*c* and 152*d* (one at a time) to fill empty supply container or bags connected to lines 152*a* or 152*b*, after which fresh dialysis fluid is pumped to the patient via serpentine heating pathway 140 via patient line 154. This procedure ensures that the accurate pump direction is used to deliver fluid to patient via the inline heater regardless of which supply container or bag is used. Container or bags 152*a* and 152*b* are emptied to drain prior to bags 152*c* and 152*d* being needed for treatment. Reverse pumping for micropump head 110, although not accurate across flow and pressure boundary conditions, is nevertheless available for pumping in situations in which flow and pressure accuracy is not important. When pumping in the accurate direction using micropump head 110, a signal from outlet pressure sensor 102*b* to control unit 50 is used as feedback to ensure that fresh dialysis fluid positive pressure to the patient is at or within a limit, e.g., 3 psig out of a range of 1.5 psig to 9 psig.

In FIG. 4, for a patient drain, used dialysis fluid is pulled from the patient, though patient line 154, inlet pressure sensor 102*a*, micropump head 110, outlet pressure sensor 102*b*, and drain line 158 leading to a drain container or house drain. The signal from inlet pressure sensor 102*a* to control unit 50 is used as feedback to ensure that used dialysis fluid negative pressure to pull from the patient is at or within a limit, e.g., −1.5 psig.

It should be appreciated that for both patient fills and drains in the embodiment of system 10 in connection with FIG. 4, fresh and used dialysis fluid flows through micropump head 110 in the same direction, which allows for the micropump to only have to be accurate in one direction. The micropump including micropump head 110 can pump in either direction in one embodiment, e.g., for bag replenishment as discussed above and in response to an occlusion as discussed below. As mentioned above, reverse pumping may be performed where a high amount of accuracy is not required. It should be appreciated that micropump head 110 as illustrated in detail in connection with FIG. 2 may be replaced in the system 10 of FIG. 4 with the piston and cylinder micropump, e.g., the Swissinova Tpump or the Swissinova Nao Stedi pump discussed above, which are likewise operated under control of control unit 50.

Figure 5:
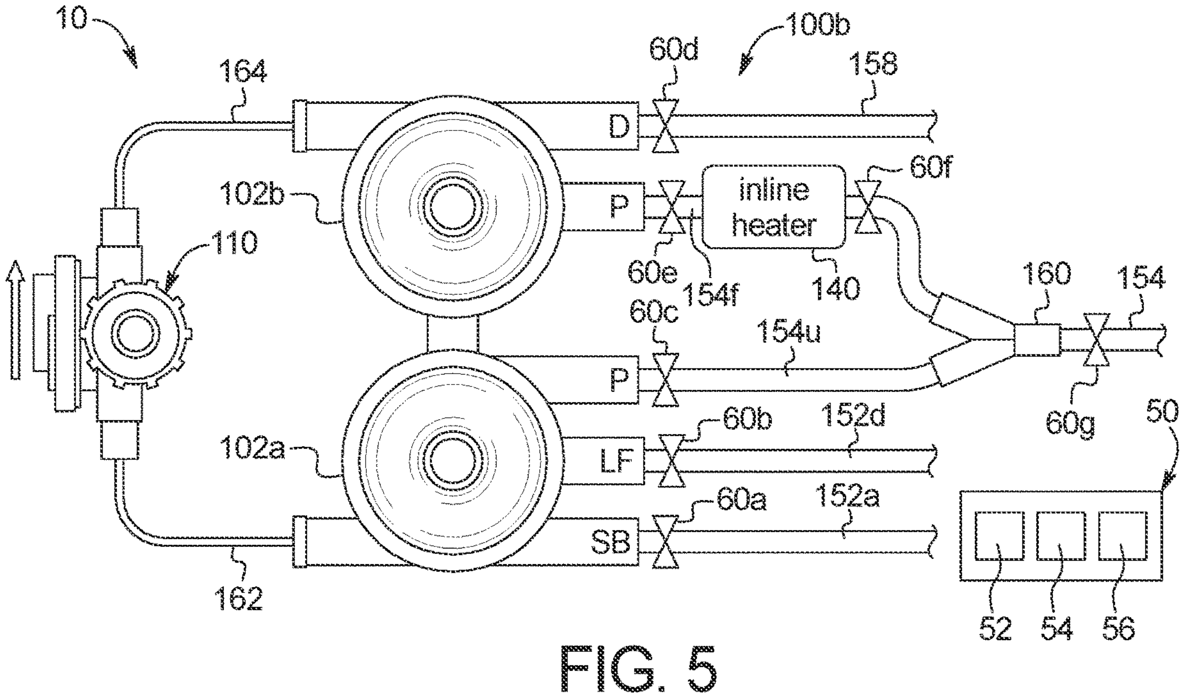
FIG. 5 is a plan view of a further embodiment for a disposable set for the APD cycler of the present disclosure, wherein the disposable set is configured for operation with pinch valves for tubing occlusion.

Referring now to FIG. 5, an alternative disposable set 100*b* for use with system 10 is illustrated. Disposable set 100*b* may be mounted for operation to cycler 20 in any of the manners discussed above in connection with FIG. 3. The primary difference between disposable set 100*b* and disposable set 100*a* is that disposable set 100*b* is configured to operate with electromechanical pinch valves 60*a* to 60*g* as opposed to the stopcock valves described above. Electromechanical pinch valves 60*a* to 60*g* operating under control of control unit may be motorized pinch valves or solenoid pinch valves, either of which may fail closed upon loss of power, so that all fluid lines close safely. Electromechanical pinch valves 60*a* to 60*g* are reusable and located within cycler 20.

Disposable set 100*b* includes fluid-contacting micropump head 110 and first and second disposable, pressure sensors or pods 102*a* and 102*b*, including all of their structure, functionality and alternatives described herein. Pressure sensor 102*a* is again an inlet pressure sensor that monitors a negative incoming fresh dialysis fluid pressure from supply line 152*a* (connected fluidly to a supply container), last fill line 152*d* (connected fluidly to a last fill container) and a negative incoming used dialysis fluid pressure from a used fluid patient line 154*u*. Pressure sensor 102*b* is again an outlet pressure sensor that monitors a positive outgoing fresh dialysis fluid pressure through fresh fluid patient line 154*f* and a positive outgoing used dialysis fluid pressure through drain line 158.

In the illustrated embodiment, disposable set 100*b* provides a Y- or T-connector 160 that fluidly merges fresh patient line 154*f* and used patient line 154*u* into a common patient line 154 that leads to the patient's catheter set. Inline fluid heating pathway 140 is illustrated in block form as being located along fresh patient line 154*f*. Pinch valve 60*a* selectively opens or occludes supply line 152*a*. Pinch valve 60*b* selectively opens or occludes last fill line 152*d*. Pinch valve 60*c* selectively opens or occludes used fluid patient line 154*u*. Pinch valve 60*d* selectively opens or occludes drain line 158. Pinch valve 60*e* selectively opens or occludes fresh fluid patient line 154*f* upstream from fluid heating pathway 140. Pinch valve 60*f* selectively opens or occludes fresh fluid patient line 154*f* downstream from fluid heating pathway 140. Pinch valve 60*g* selectively opens or occludes common patient line 154.

Fluid-contacting micropump head 110 communicates fluidly with (i) the outlet from pressure sensor 102*a* via pump inlet line 162 and (ii) the inlet to pressure sensor 102*b* via pump outlet line 164. In FIG. 5, for a patient fill, fresh dialysis fluid flows from supply lines 152 or last fill line 152*d*, through inlet pressure sensor 102*a*, pump inlet line 162, micropump head 110, pump outlet line 164, outlet pressure sensor 102*b*, fresh fluid patient line 154*f* and serpentine heating pathway 140, Y- or T-connector 160 and common patient line 154 to the patient. Here, one of pinch valve 60*a* or 60*b* is open and valves 60*e* to 60*g* are open, while the other one of valves 60*a* or 60*b*, valve 60*c* and drain valve 60*d* are closed. The signal from outlet pressure sensor 102*b* to control unit 50 is used as feedback to ensure that fresh dialysis fluid positive pressure to the patient is at or within a limit, e.g., 3 psig.

In FIG. 5, for a patient drain, used dialysis fluid is pulled from the patient, through common patient line 154, Y- or T-connector 160, used fluid patient line 154*u*, inlet pressure sensor 102*a*, pump inlet line 162, micropump head 110, pump outlet line 164, outlet pressure sensor 102*b*, and drain line 158 leading to a drain container or house drain. The signal from inlet pressure sensor 102*a* to control unit 50 is used as feedback to ensure that used dialysis fluid negative pressure to pull from the patient is at or within a limit, e.g., −1.5 psig.

It should be appreciated that for both patient fills and drains in the embodiment of system 10 in connection with FIG. 5, fresh and used dialysis fluid flows through micropump head 110 in the same direction, which again allows for the micropump (which can pump in both directions) to only have to be accurate in one direction. It should be appreciated that micropump head 110 as illustrated in detail in connection with FIG. 2 may be replaced in the system 10 of FIG. 5 with the piston and cylinder micropump, e.g., the Swissinova Tpump or the Swissinova Nao Stedi pump, discussed above, which are likewise operated under control of control unit 50.

Figure 6:
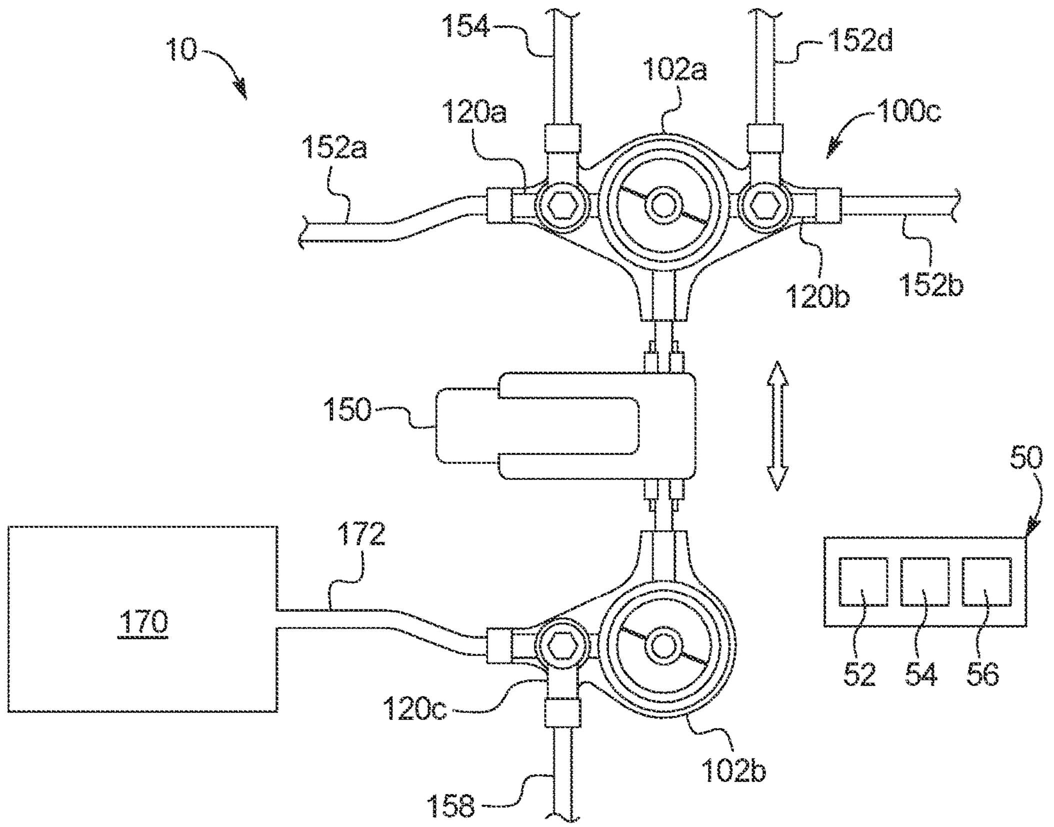
FIG. 6 is a plan view of another embodiment for a disposable set for the APD cycler of the present disclosure, wherein the disposable set is configured for operation with batch heating and a micropump that is accurate in two directions.

Referring now to FIG. 6, another alternative disposable set 100*c* for use with system 10 is illustrated. Disposable set 100*c* may be mounted for operation to cycler 20 in any of the manners discussed above in connection with FIG. 3. The primary difference between disposable set 100*c* and disposable set 100*a* is that disposable set 100*c* is configured to operate with a heater container or bag 170 via a heater bag line 172 for batch heating instead of inline heating. Another difference is that the micropump having an alternative fluid-contacting micropump head 150 pumps accurately in two directions, and may be a piston and cylinder type micropump, e.g., Swissinova Tpump, discussed above, operated under control of control unit 50. It should be appreciated that the batch heating of the present disclosure does not require pumping accuracy in two directions, rather, the example disposable set 100*c* of FIG. 6 illustrates that system may be operated with such capability.

Fluid-contacting micropump head 150 is located between first and second disposable, pressure sensors or pods 102*a* and 102*b*. Pressure sensor 102*a* is located fluidly between first and second three-way disposable, fluid-contacting stopcock valve portions 120*a* and 120*b*. Pressure sensor 102*b* is in fluid communication with a third three-way disposable, fluid-contacting stopcock valve portion 120*c*. Three-way valve portion 120*a* provides alternative fluid communication with the patient via patient line 154 or a first supply line 152*a* leading to a first supply container, e.g., bag. Three-way valve portion 120*b* provides alternative fluid communication with a second supply line 152*b* leading to a second supply container, e.g., bag, or a last fill line 152*d*, which is connected to a last fill dialysis fluid supply container (e.g., bag, last fill for extended dwell). Three-way valve portion 120*c* provides alternative fluid communication with heater bag 170 via a heater bag line 172 or drain line 158 leading to a drain container (e.g., bag) or house drain (e.g., toilet or bathtub).

Using disposable set 100*c*, control unit 50 of system 10 for a patient fill manipulates three-way valve portions 120*a* and 120*b* and actuates micropump head 150 so as to draw fresh dialysis fluid or last fill fluid from its respective source and push same to heater bag 170, where a resistive plate and/or radiant or other heater heats the batch of fresh dialysis fluid to body temperature, e.g., 37° C. Once heated, control unit 50 manipulates three-way valve portions 120*a* to 120*c* and actuates micropump head 150 so as to draw fresh, heated dialysis fluid from heater bag 170 and push same in the reverse direction to the patient via patient line 154. While it is beneficial to be accurate in both directions so as not to overfill or underfill heater bag 170, it is more important to be accurate pumping in the second direction to provide a prescribed fill volume to the patient.

During a patient dwell phase using disposable set 100*c*, control unit 50 causes a second batch of dialysis fluid to be heated in heater bag 170 via the sequence described above.

Using disposable set 100*c*, control unit 50 of system 10 for a patient drain manipulates three-way valve portions 120*a* and 120*c* and actuates micropump head 150 so as to draw used dialysis fluid from the patient via patient line 154 and push same to a drain container or house drain via drain line 158. It is important in the patient drain to be accurate to know how much effluent has been removed from the patient, so that an accurate amount of ultrafiltration ("UF") removed from the patient is calculated by control unit subtracting the fill volume from the drain volume.

One possible way to use a micropump that is accurate in one direction with batch heating is to move drain line 158 and the drain to one of supply lines 152*a* or 152*b* and make the remaining supply container larger. The now empty port of three-way valve portions 120*c* is then connected to an empty sample container, which initially receives a patient drain from a non-accurate flow direction. Next, control unit 50 causes a second batch of heated, fresh dialysis fluid to be pumped in an accurate direction to the patient via patient line 154. After the second patient fill, control unit 50 causes the drain fluid to be pumped from the sample container in the accurate direction to drain via drain line 158. After the removal of effluent to drain, control unit 50 causes a next patient fill volume, e.g., last fill volume, to be pumped to heater bag 170 for a subsequent patient fill.

Figure 7A:
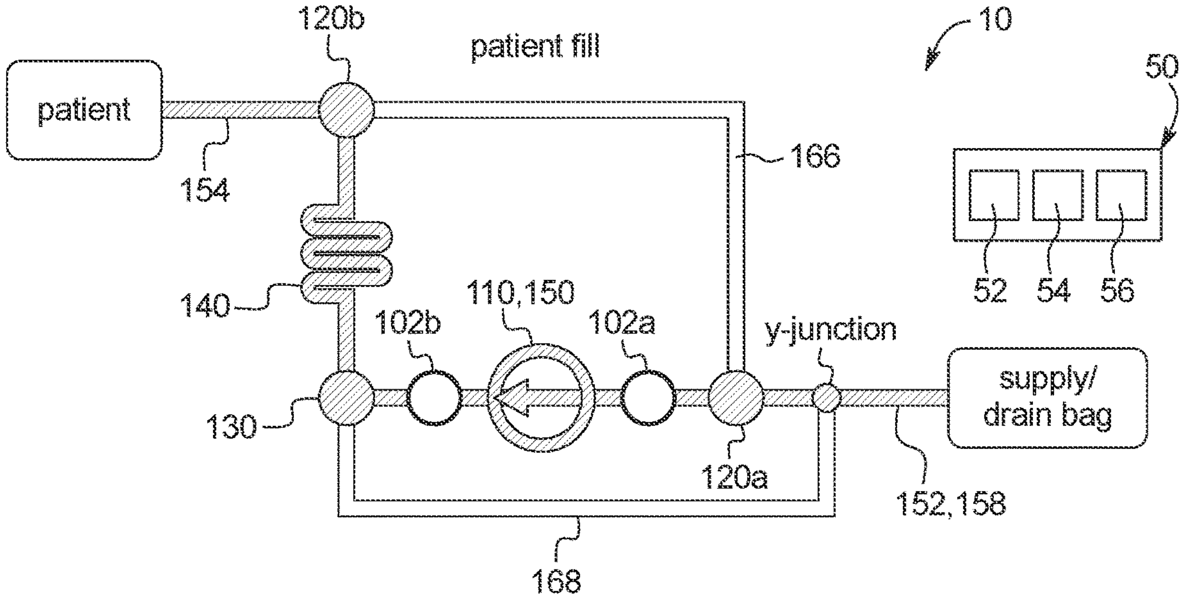
FIG. 7A is a schematic view illustrating one embodiment for a patient fill using a micropump of the present disclosure.
Figure 7B:
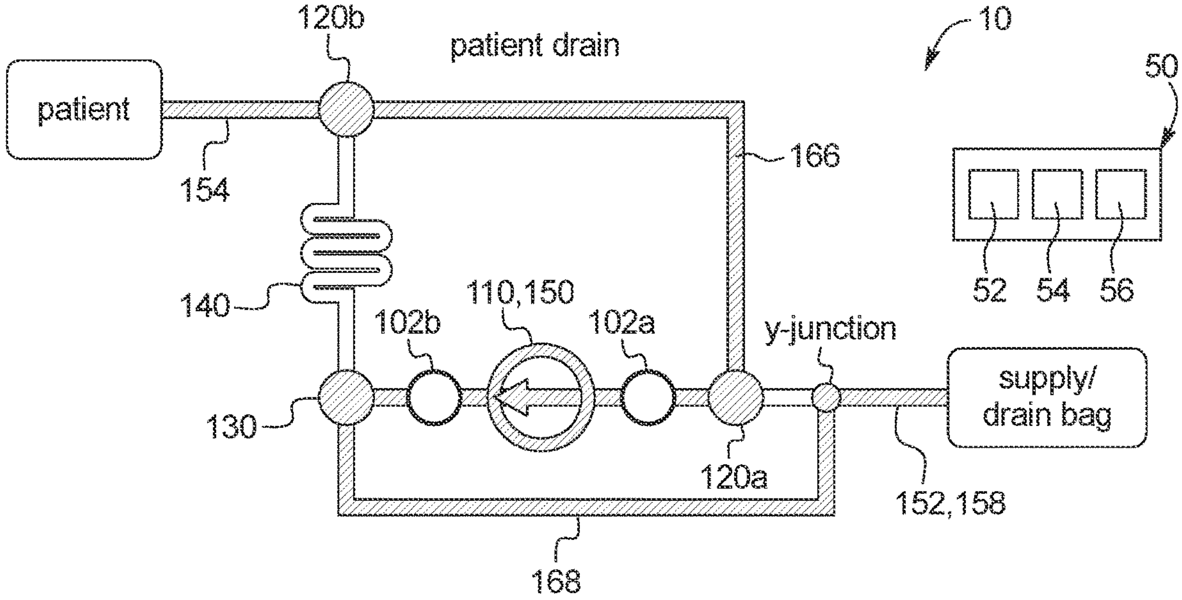
FIG. 7B is a schematic view illustrating one embodiment for a patient drain using a micropump of the present disclosure.

Referring now to FIGS. 7A and 7B, one possible patient fill flow regime and patient drain regime, respectively, for a disposable set, such as set 100*a*, having a combination of three-way disposable, fluid-contacting stopcock valve portions 120*a* and 120*b* and a three-way disposable, fluid-contacting stopcock valve portion 130 is illustrated. Inlet and outlet pressure sensors or pods 102*a* and 102*b* located on either side of micropump having disposable, fluid-contacting micropump head 110 or 150 are also provided. Inline fluid heating pathway 140 in fresh dialysis fluid line is also provided. For convenience, the supply and drain containers are illustrated as the same containers communicating with common supply and drain line 152, 158, which is contemplated to reduce disposable waste and cost. The supply and drain containers are alternatively separate. Patient line 154 leads to the patient. Additional lines 166 and 168 used for the patient drain are also provided.

In FIG. 7A using disposable set 100*a*, control unit 50 of system 10 for a patient fill manipulates three-way valve portions 120*a* and 120*b* and three-way valve portion 130 and actuates micropump head 110 or 150 so as to draw fresh dialysis fluid or last fill fluid from its respective source via common supply and drain line 152, 158 and push same through inline fluid heating pathway 140, where a resistive plate and/or radiant or other heater heats the fresh dialysis fluid to body temperature, e.g., 37° C. The inline flow of now heated fresh dialysis then flows to the patient via patient line 154. Control unit 50 uses the signal from pressure sensor 102*b* to ensure that fresh dialysis fluid positive pressure to the patient is at or within a limit, e.g., 3 psig.

Regarding the inline heating of system 10, preliminary data have shown positive results. The data demonstrates the flow profile from micropump head 110 or 150 in combination with the dampening discussed herein is suitable, e.g., continuous enough, to be used with inline heating and to deliver fresh, heated dialysis fluid to the patient in an accurate manner.

In FIG. 7B using disposable set 100*c*, control unit 50 of system 10 for a patient drain manipulates three-way valve portions 120*a* and 120*b* and three-way valve portion 130 and actuates micropump head 110 or 150 so as to draw used dialysis fluid from the patient via patient line 154 and line 166 and push same through line 168 and common supply and drain line 152, 158 to drain container or bag 152, 158. Control unit 50 uses the signal from pressure sensor 102*a* to ensure that used dialysis fluid negative pressure to pull effluent from the patient is at or within a limit, e.g., −1.5 psig.

It should be appreciated that for both patient fills and drains in the embodiment of system 10 in connection with FIGS. 7A and 7B, fresh and used dialysis fluid flows through micropump head 110 or 150 in the same direction, which allows for the micropump to only have to be accurate in one direction.

As discussed above and as illustrated below in connection with FIGS. 11A, 11B, 12A, 12B, 13A and 13B, pressure sensors or pods 102*a* and 102*b* have been found to dampen the pulsatility of the micropumps of the present disclosure. Another solution contemplated for system 10 and associated methodology of the present disclosure for alternatively or additionally managing the pulsatile nature of the micropumps is to employ flowrate profiles. The peritoneal dialysis treatment of the present disclosure includes the cyclical introduction and removal of dialysis fluid to and from the patient's peritoneal cavity. Excess pressure in either direction may cause patient discomfort. System 10 and associated methodology however capitalize on the phenomenon that the patient is most susceptible to discomfort at the beginning and end of both patient fills and patient drains. During the middle of both the fills and drains, patient discomfort is less likely and/or less intense.

It is accordingly contemplated to program control unit 50 to store flowrate profiles that cause the micropump having fluid portion 110 or 150 to begin a patient fill or drain at a lower flowrate until a certain amount of fresh or used dialysis fluid is delivered to or removed from the patient, e.g., the first ten percent of a total fill or drain volume. After the initial defined amount of fresh or used dialysis fluid is delivered or removed, control unit 50 running the appropriate profile causes the micropump having fluid portion 110 or 150 to ramp the flowrate up to full speed according to a desired acceleration curve, e.g., linear or sinusoidal. At a certain point near the end of the fill or drain, e.g., the last ten percent, control unit 50 running the appropriate profile causes the micropump having fluid portion 110 or 150 to ramp the flowrate down to the same or different lower flowrate according to a desired deceleration curve, e.g., linear or sinusoidal. The system and methodology of the present disclosure may employ the flowrate profiles alone or in combination with pressure dampeners or pressure sensors or pods 102*a* and 102*b* to address the pulsatile input and output nature of the micropumps of the present disclosure.

Figure 8:
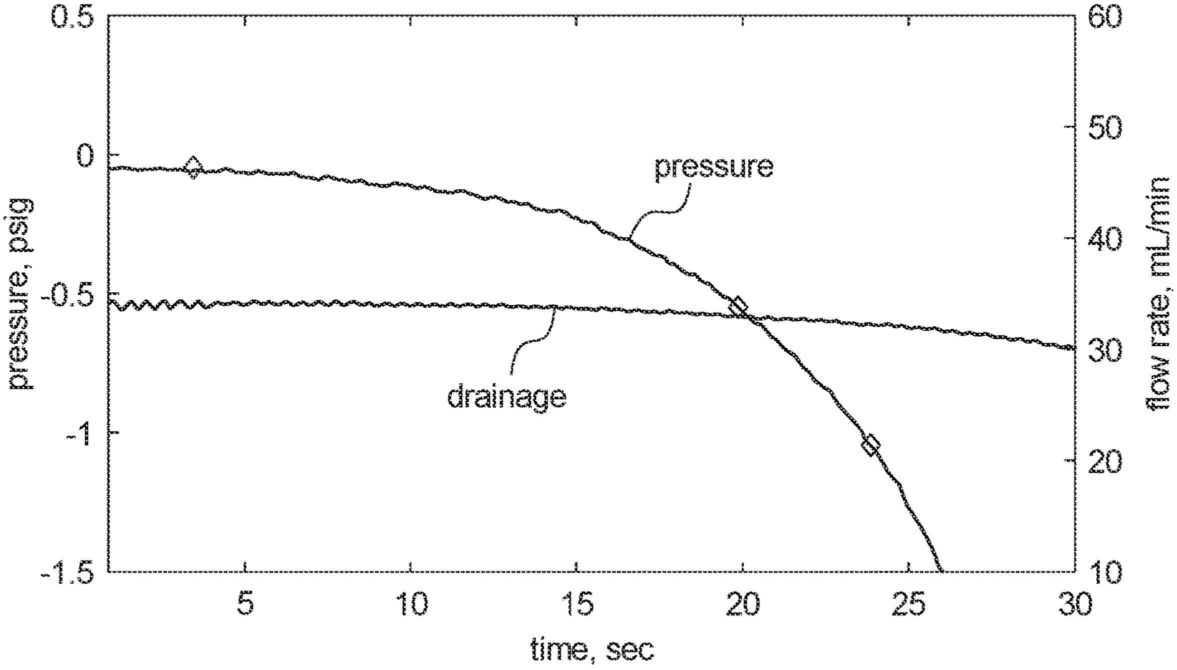
FIG. 8 is a plot illustrating one embodiment for patient empty detection using the micropump APD system and method of the present disclosure.

Referring now to FIG. 8, an example plot illustrates that at a drain flowrate (labeled "drainage") of about 34 mL/min, the patient becomes close to empty as the micropump, e.g., using micropump head 110, tries to maintain a constant flowrate by increasing suction at its inlet owing to increased catheter resistance. The negative pressure increase (labeled "pressure") as measured by the pressure sensor or pods 102*a* or 102*b* located between micropump head 110 is detected by control unit 50, which is programmed to look for such negative pressure increase during the patient drain. For example, control unit 50 for any of the versions of system 10 discussed herein may be programmed to look for the negative pressure to (i) reach a certain limit, (ii) change at a certain rate or slope, or (iii) combinations thereof. Once the limit or criterion is reached, control unit 50 causes the patient drain to stop. Control unit 50 notes the volume of the drain for use in determining UF as discussed above.

It should be noted that the treatment algorithm stored on control unit 50 may employ checks for occlusion before a patient drain is considered complete or that the patient is considered to be empty enough to stop the current drain phase.

Figure 9:
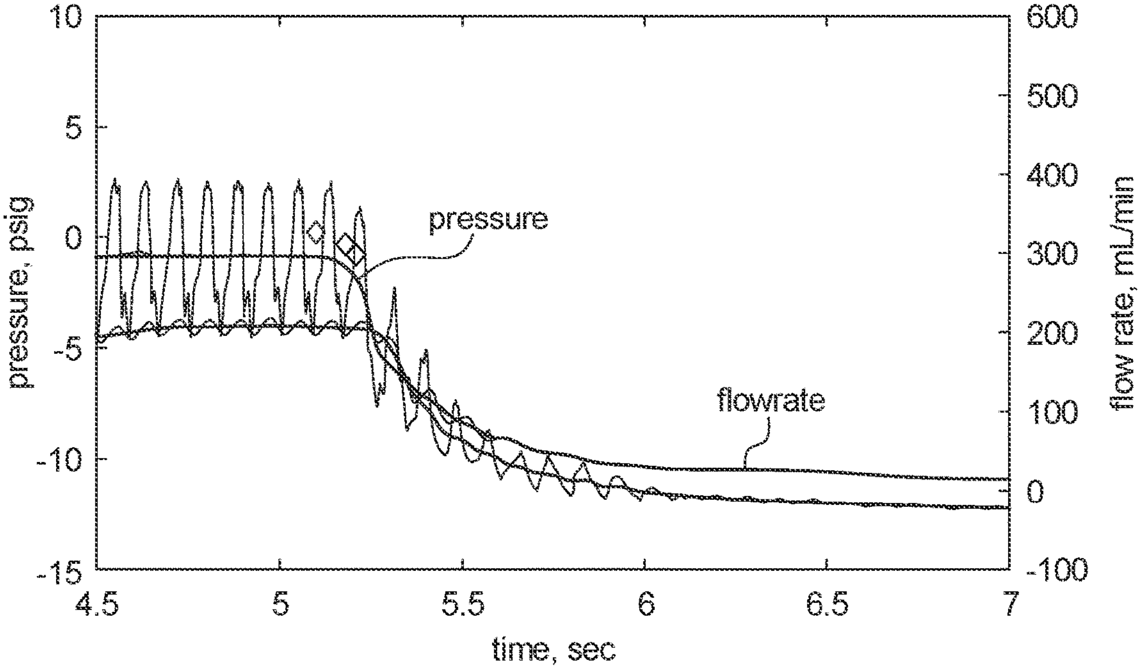
FIG. 9 is a plot illustrating one embodiment for drain occlusion detection using the micropump APD system and method of the present disclosure.

Referring now to FIG. 9, an example plot illustrates the detection of a negative pressure drain occlusion in patient line 154 during a patient drain using any version of system 10 discussed herein, e.g., using micropump head 110. Here, when patient line 154 becomes kinked, the flowrate (labeled "flowrate") drops and the negative suction pressure (labeled "pressure") increases (becomes more negative). The pressure change is measured by the pressure sensor 102*a* or 102*b* located between micropump head 110 and patient line 154 and is outputted to control unit 50, which is programmed to look for the flowrate drop and/or negative pressure increase. For example, control unit 50 for any of the versions of system 10 discussed herein may be programmed to look for a combination of (i) the flowrate dropping only (to a threshold level and/or over a certain rate of change), (ii) the negative pressure increasing only (to a threshold level and/or over a certain rate of change) in combination with the negative pressure increase occurring at a time unlikely to be and end of drain, or (iii) the flowrate dropping (to a threshold level and/or over a certain rate of change) in combination with the negative pressure increasing (to a threshold level and/or over a certain rate of change). Once any of (i) to (iii) above is triggered, control unit 50 determines an occlusion and sounds an alarm, perhaps after pushing fluid back towards the patient to confirm the occlusion. Control unit 50 also notes the volume of the drain up until the occlusion. Control unit may also cause user interface 60 to display an audio, visual or audiovisual message showing the patient how to clear the occlusion so that the patient drain may resume.

It should be noted that since the embodiments illustrated herein do not directly measure flowrate other than expected stroke volume discussed herein, pressure decay is the indicator for negative pressure drain occlusion. It is contemplated in alternative embodiments to add one or more flow sensor outputting to control unit 50 in any of the implementations discussed hereon. Here, the flowrate sensor output may be used alternatively to or additionally with the pressure decay the indicator for negative pressure drain occlusion just described.

Figure 10:
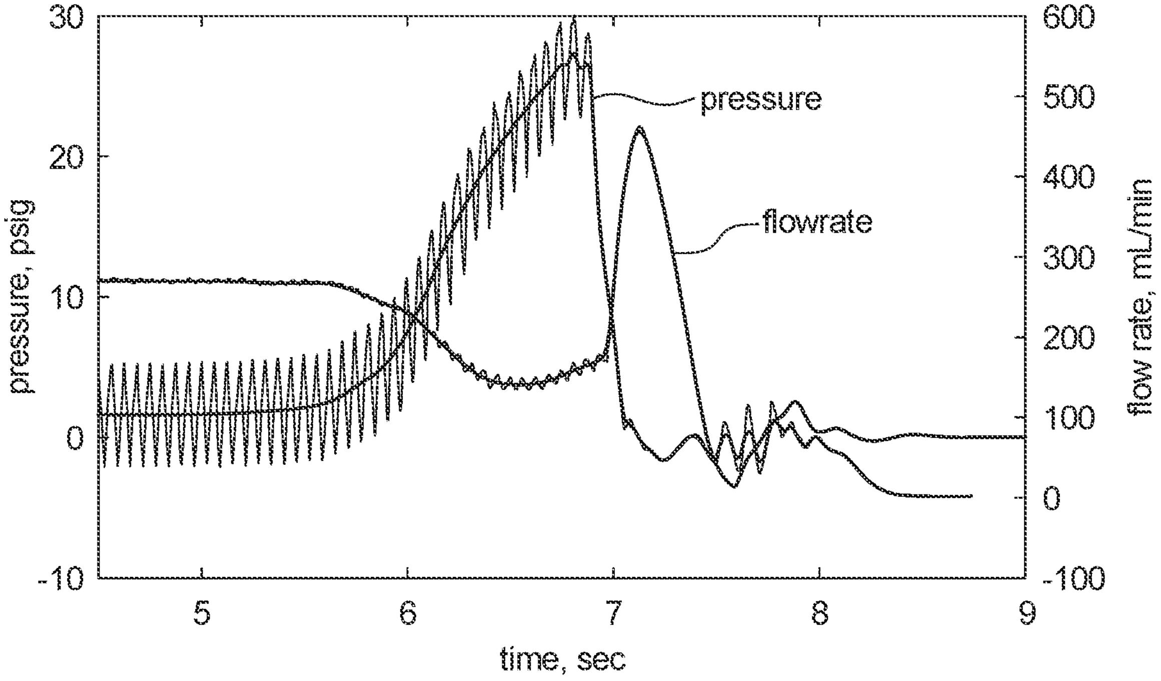
FIG. 10 is a plot illustrating one embodiment for fill occlusion detection using the micropump APD system and method of the present disclosure.

Referring now to FIG. 10, an example plot illustrates the detection of a positive pressure occlusion in patient line 154 during a patient fill using any version of system 10 discussed herein, e.g., using micropump head 110. Here, when patient line 154 becomes kinked, the flowrate (labeled "flowrate") drops and the positive fill pressure (labeled "pressure") spikes (becomes more positive). The pressure change is again measured by pressure sensor 102*a* or 102*b* located between fluid micropump portion 110 and patient line 154 and is outputted to control unit 50, which is programmed to look for the flowrate drop and/or positive pressure increase. For example, control unit 50 for any of the versions of system 10 discussed herein may be programmed to look for a combination of (i) the flowrate dropping only (to a threshold level and/or over a certain rate of change), (ii) the positive pressure increasing only (to a threshold level and/or over a certain rate of change), or (iii) the flowrate dropping (to a threshold level and/or over a certain rate of change) in combination with the positive pressure increasing (to a threshold level and/or over a certain rate of change). Once any of (i) to (iii) above is triggered, control unit 50 determines an occlusion and sounds an alarm, perhaps after pushing fluid back towards the patient to confirm the occlusion. Control unit 50 also notes the volume of the fill up until the occlusion. Control unit may also cause user interface 60 to display an audio, visual or audiovisual message showing the patient how to clear the occlusion so that the patient fill may resume.

As illustrated above, micropump system 10 provides certain advantages regarding empty and occlusion detection. Empty and occlusion detection based on pressure decay or rise as described herein provides quick results. Partial occlusions, which may result in slower flowrates in other types of APD systems, do not affect micropump system 10 similarly, because the micropump system is able to maintain required flowrates even with the partial occlusion due to its higher pressure vs accuracy capability, thereby maintaining a prescribed treatment time or improving treatment time compared to other types of systems.

Figure 11A:
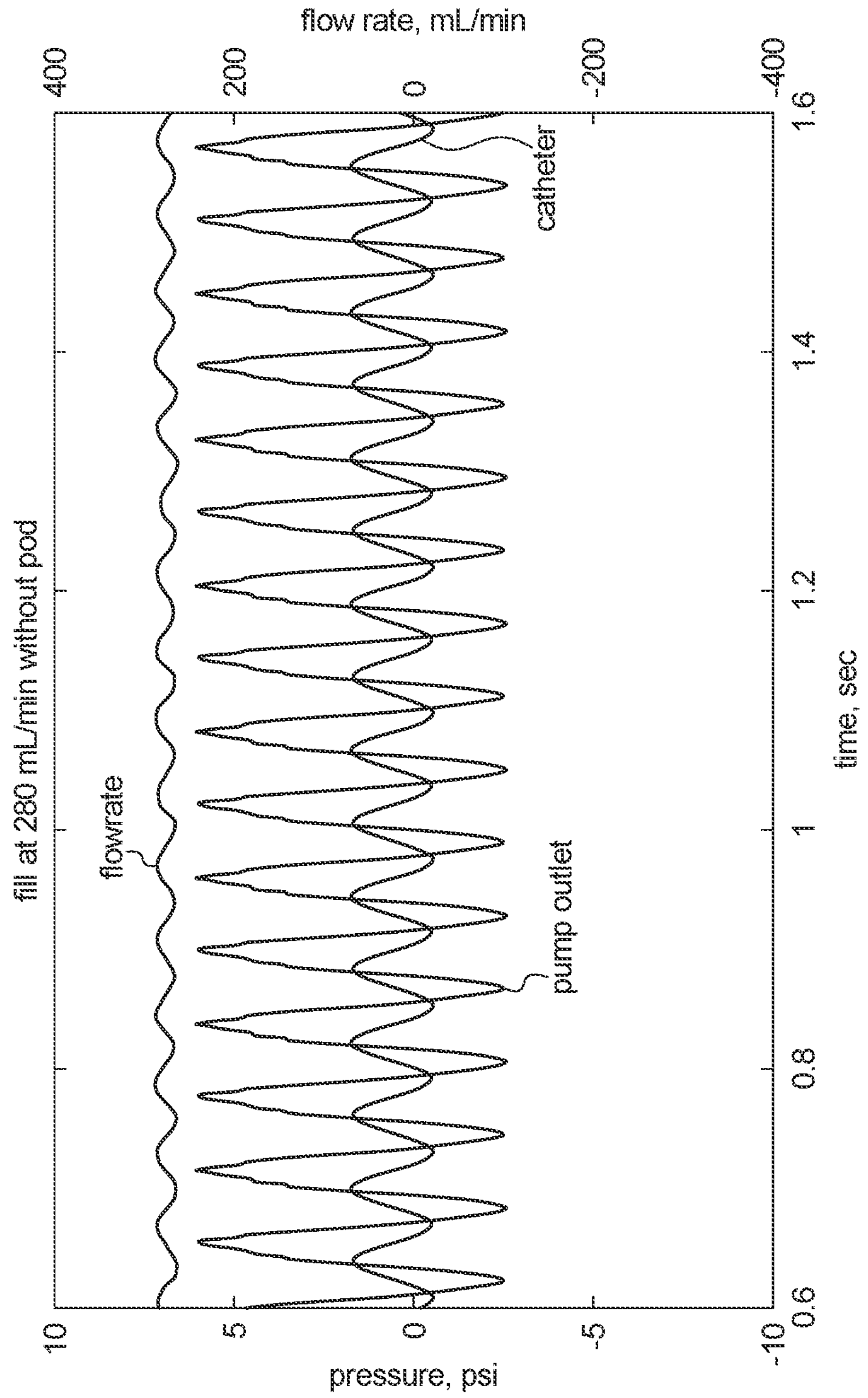
FIGS. 11A and 11B are plots illustrating the use of the micropump APD system and method of the present disclosure, which show the effects of pressure pod dampening for a larger patient fill flowrate.
Figure 11B:
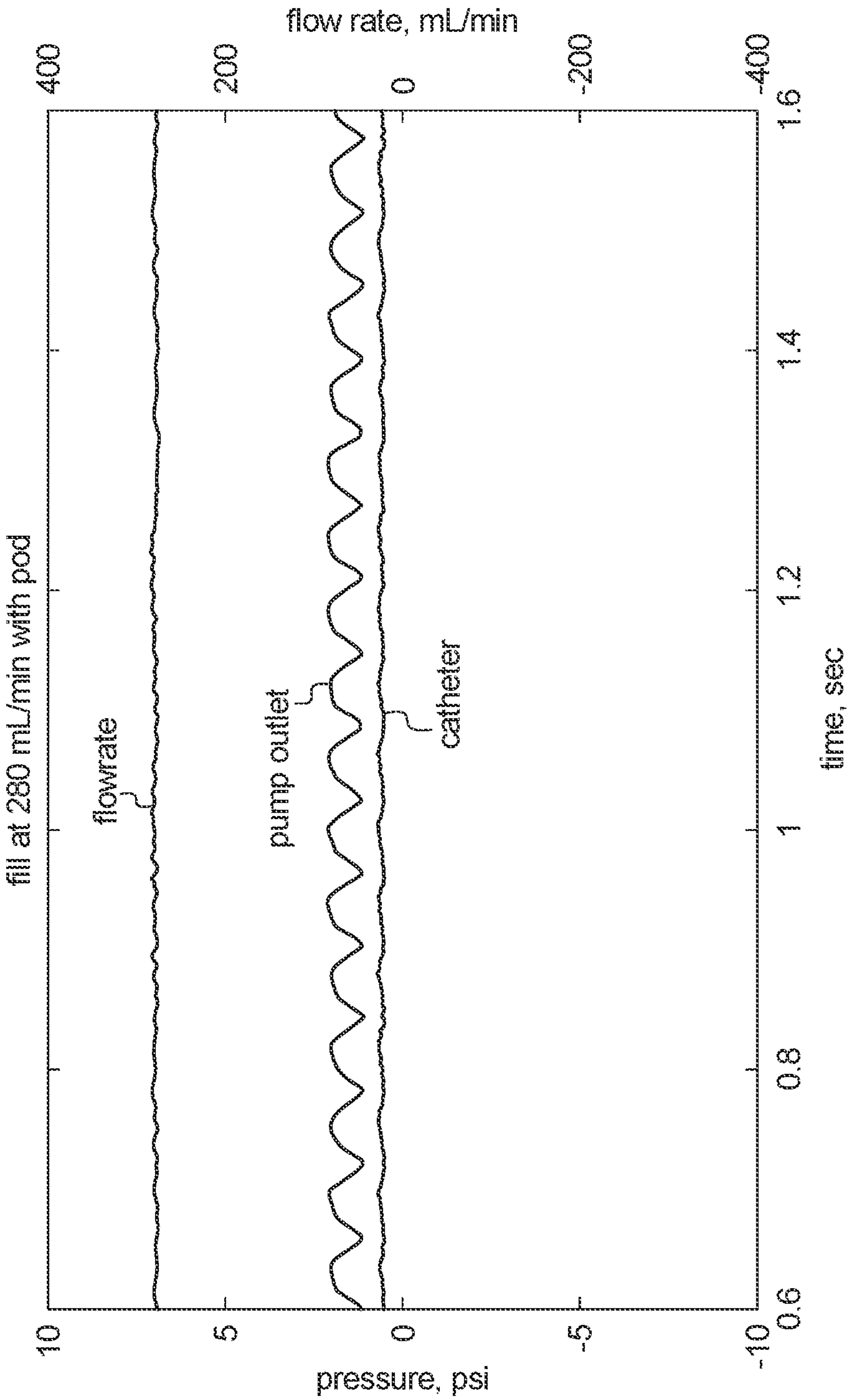

Regarding the dampening effects of pressure pods 102*a* and 102*b* discussed herein, FIGS. 11A and 11B illustrate the beneficial dampening effects for a larger patient fill flowrate of 280 mL/min. The curves of FIG. 11A are for actuation of the micropump without a pressure pod 102*a* or 102*b*, while the curves of FIG. 11B are for actuation of the micropump with a pressure pod 102*a* or 102*b*. The plots of FIGS. 11A and 11B each show three curves, namely, a "flowrate" curve, a "pump outlet" curve that shows pressure measurements taken at 0.3 meters from an outlet of micropump head 110, and a "catheter" curve that shows pressure measurements taken at 0.5 meters from a patient's indwelling catheter. FIG. 11B illustrates that the fill flowrate at 280 mL/min is relatively constant and is a great deal more constant than the fill flowrate at 280 mL/min in FIG. 11A. The amplitudes of the pump outlet pressure curve of FIG. 11B at 280 mL/min are quarter or less than the amplitudes of the pump outlet pressure curve of FIG. 11A at 280 mL/min. Likewise, the amplitudes of the catheter pressure curve of FIG. 11B at 280 mL/min are virtually flat relative to the amplitudes of the catheter pressure curve of FIG. 11A at 280 mL/min. FIGS. 11A and 11B illustrate that pressure pods 102*a* or 102*b* have a significant impact on dampening the pulsatile output of the micropumps of the present disclosure while filling the patient at 280 mL/min.

Figure 12A:
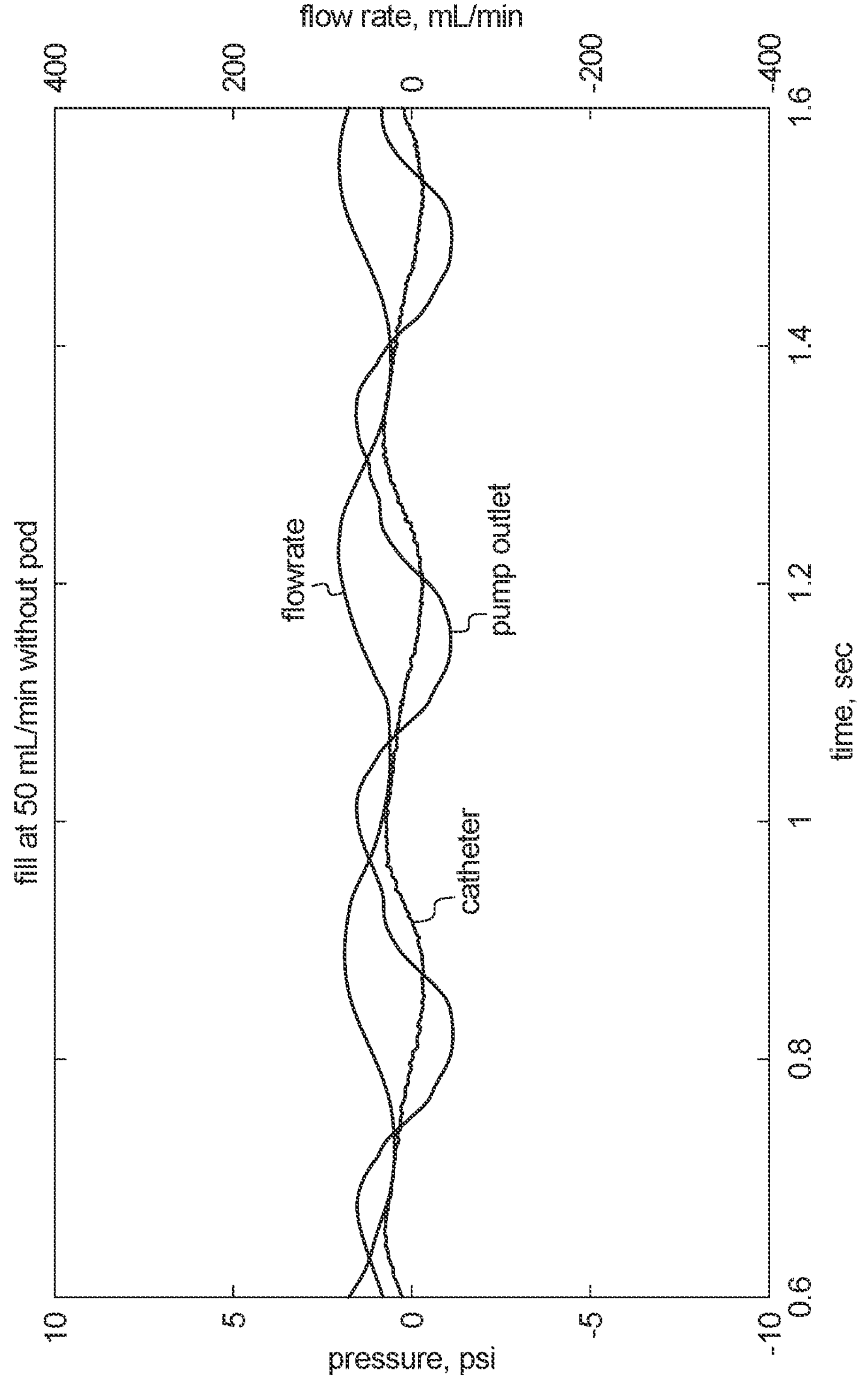
FIGS. 12A and 12B are plots illustrating the use of the micropump APD system and method of the present disclosure, which show the effects of pressure pod dampening for a low patient fill flowrate.
Figure 12B:
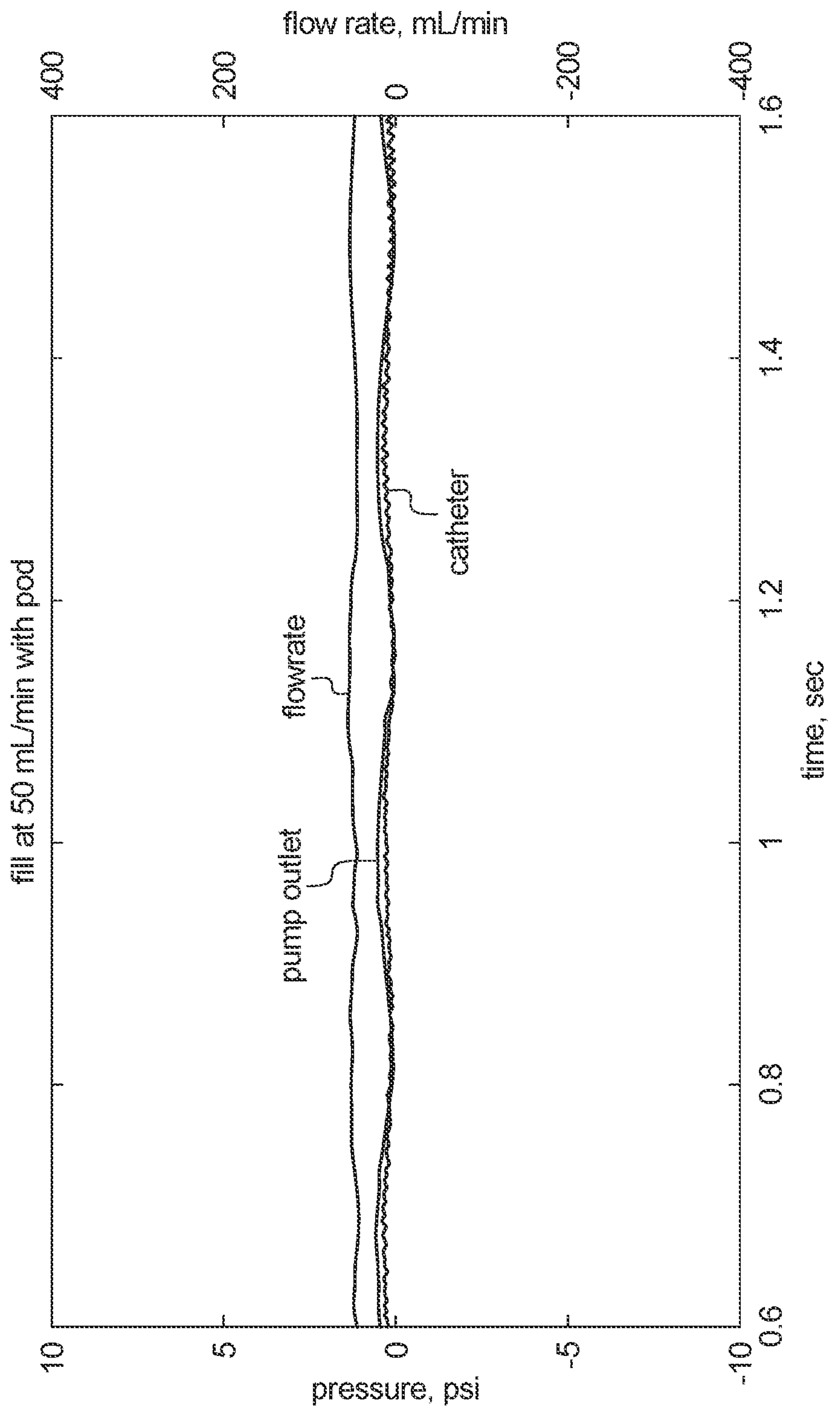

FIGS. 12A and 12B illustrate the beneficial dampening effects for a low patient fill flowrate of 50 mL/min (e.g., at the end of a patient fill or for a pediatric patient fill). The curves of FIG. 12A are for actuation of the micropump without a pressure pod 102*a* or 102*b*, while the curves of FIG. 12B are for actuation of the micropump with a pressure pod 102*a* or 102*b*. The plots of FIGS. 12A and 12B show the same three "flowrate" curve, "pump outlet" curve and "catheter" curve described above for FIGS. 11A and 11B. FIG. 12B illustrates that the fill flowrate at 50 mL/min is relatively constant and a great deal more constant than the fill flowrate at 50 mL/min in FIG. 12A. The amplitudes of the pump outlet pressure curve of FIG. 12B at 50 mL/min are virtually flat relative to the amplitudes of the pump outlet pressure curve of FIG. 12A at 50 mL/min. Likewise, the amplitudes of the catheter pressure curve of FIG. 12B at 50 mL/min are virtually flat relative to the amplitudes of the catheter pressure curve of FIG. 12A at 50 mL/min. FIGS. 12A and 12B illustrate that pressure pods 102*a* or 102*b* have a significant impact on dampening the pulsatile output of the micropumps of the present disclosure while filling the patient at 50 mL/min.

Figure 13A:
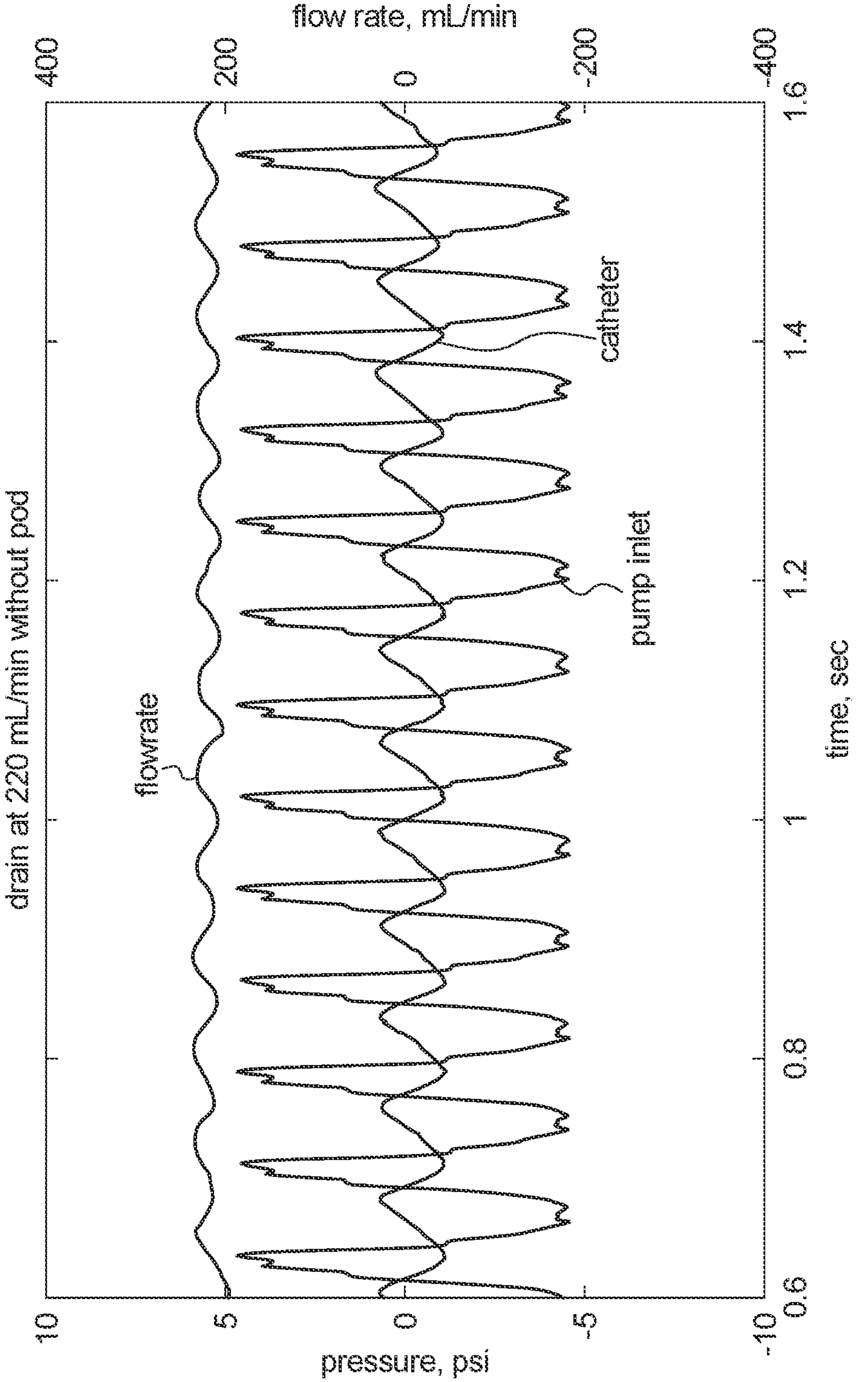
FIGS. 13A and 13B are plots illustrating the use of the micropump APD system and method of the present disclosure, which show the effects of pressure pod dampening for a larger patient drain flowrate.
Figure 13B:
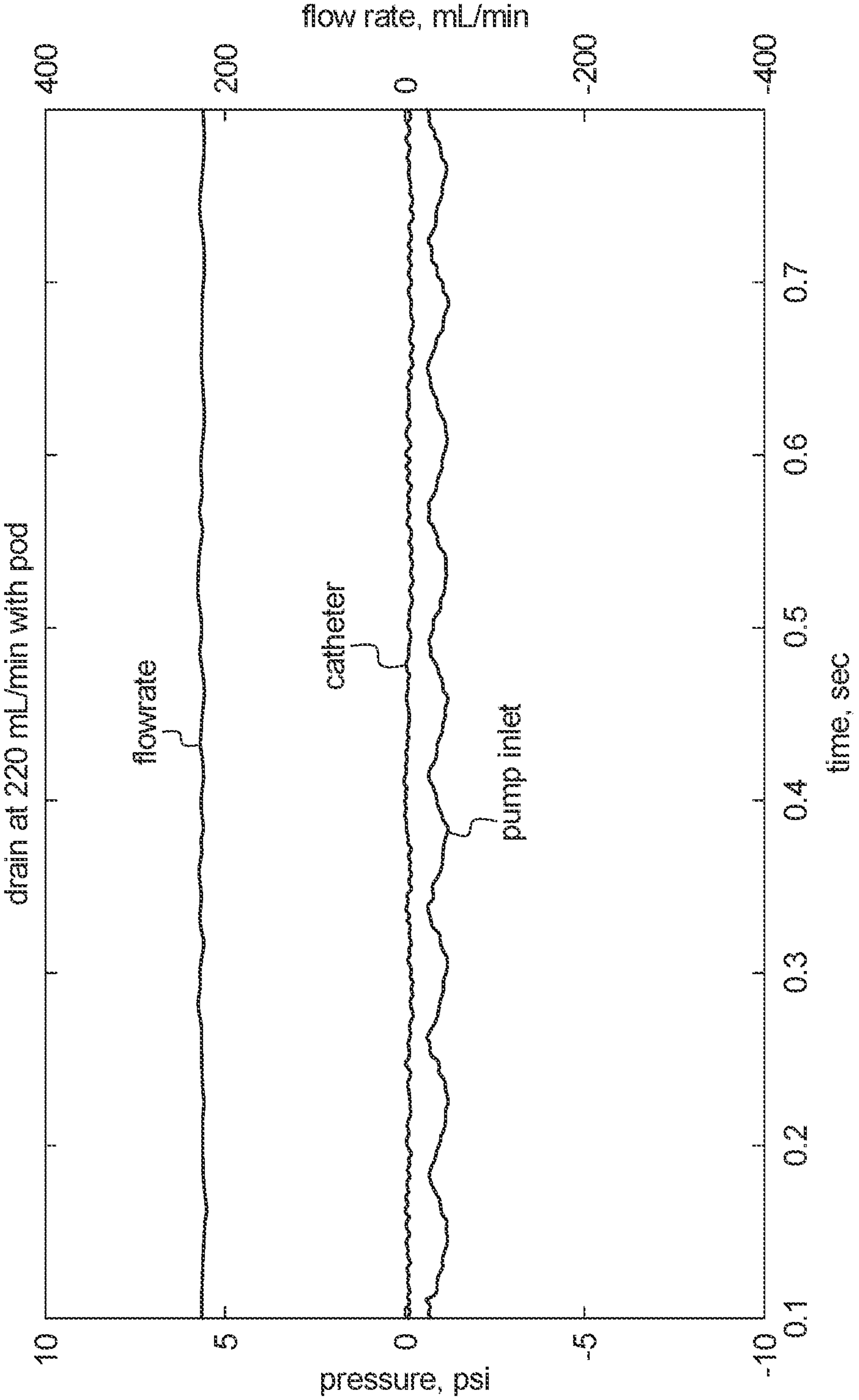

FIGS. 13A and 13B illustrate the beneficial dampening effects for a larger patient drain flowrate of 220 mL/min. The curves of FIG. 13A are for actuation of the micropump without a pressure pod 102*a* or 102*b*, while the curves of FIG. 13B are for actuation of the micropump with a pressure pod 102*a* or 102*b*. The plots of FIGS. 13A and 13B show three "flowrate" curve, "pump inlet" curve and "catheter" curve described above for FIGS. 11A and 11B. FIG. 13B illustrates that the drain flowrate at 220 mL/min is relatively constant and a great deal more constant than the drain flowrate at 220 mL/min in FIG. 13A. The amplitudes of the pump inlet pressure curve of FIG. 13B at 220 mL/min are a quarter or less than the amplitudes of the pump inlet pressure curve of FIG. 13A at 220 mL/min. Likewise, the amplitudes of the catheter pressure curve of FIG. 13B at 220 mL/min are virtually flat relative to the amplitudes of the catheter pressure curve of FIG. 13A at 220 mL/min. FIGS. 13A and 13B illustrate that pressure pods 102*a* or 102*b* have a significant impact on dampening the pulsatile output of the micropump while draining the patient at 220 mL/min.

It should be understood that various changes and modifications to the presently preferred embodiments described herein will be apparent to those skilled in the art. For example, instead of providing lids 26*a* and 26*b* that open to allow disposable set 100*a* to be translated down into APD cycler 20, disposable set 100*a* could instead be loaded directly onto the top of the cycler. Also, while stopcock and pinch valves have been illustrated, it is contemplated to alternatively provide cassette-based valves, such as pneumatic valves. Moreover, any of the three-way valves described herein may be replaced with multiple two-way valves. It is therefore intended that such changes and modifications be covered by the appended claims.

The invention is claimed as follows:

1. A peritoneal dialysis ("PD") system comprising:

a cycler including a micropump actuator, an inline fluid heater or batch fluid heater, a pressure transducer, and at least one valve actuator;

a disposable set including a micropump head sized and shaped for mating with and being cyclically driven by the micropump actuator, a pressure sensor configured to operably communicate with the pressure transducer, at least one fluid valve portion or a portion of at least one fluid line for interfacing with the at least one valve actuator, a fresh patient line located on a first side of the micropump head, a used patient line located on an opposite, second side of the micropump head, a Y- or T-connector connected to the fresh patient line and the used patient line, the Y- or T-connector configured to fluidly couple the fresh patient line and the used patient line to a patient line, and an inline fluid heating pathway or a batch heater container located along the fresh patient line; and a control unit, wherein the fresh patient line, the used patient line, and the Y- or T-connector of the disposable set are arranged to allow, and the control unit is programmed to operate the micropump actuator and the at least one valve actuator so that fresh and used dialysis fluid flows through the micropump head in a same direction, wherein the inline fluid heater or batch fluid heater of the cycler is positioned and arranged to heat the inline fluid heating pathway or the batch heater container of the disposable set, respectively, when the disposable set is mounted to the cycler, wherein the at least one valve actuator includes a first valve actuator located along the fresh patient line and a second valve actuator located along the used patient line when the disposable set is mounted to the cycler, wherein the control unit is configured to cause the first valve actuator to open and the second valve actuator to close so that the micropump actuator pumps the fresh dialysis fluid through the fresh patient line to the patient line, and wherein the control unit is configured to cause the second valve actuator to open and the first valve actuator to close so that the micropump actuator pumps the used dialysis fluid through the used patient line from the patient line.

2. The PD system of claim 1, wherein the micropump actuator and the micropump head are more accurate in the same direction than in a reverse direction.

3. The PD system of claim 1, wherein the micropump actuator includes a keyed driver and the micropump head includes a keyed recess sized and shaped for mating with the keyed driver of the micropump actuator.

4. The PD system of claim 1, wherein the pressure sensor includes a fluid pressure chamber having a sealed diaphragm configured to fluctuate due to pressure variations, and wherein the cycler includes a transmission fluid chamber positioned and arranged to mate with the fluid pressure chamber when the disposable set is mounted to the cycler.

5. The PD system of claim 4, wherein a transmission fluid line extends from the transmission fluid chamber to the pressure transducer.

6. The PD system of claim 1, wherein the pressure sensor includes a fluid pressure chamber having a sealed diaphragm configured to fluctuate due to pressure variations, and a transmission fluid chamber sealed to the fluid pressure chamber.

7. The PD system of claim 6, wherein the pressure sensor interfaces with the pressure transducer via a transmission fluid line placed in fluid communication with the transmission fluid chamber.

8. The PD system of claim 1, wherein the at least one fluid valve portion includes a rotating stem and the at least one valve actuator is configured to rotate the rotating stem.

9. The PD system of claim 1, wherein the at least one valve actuator is a pinch valve positioned and arranged to occlude the portion of at least one fluid line when the disposable set is mounted to the cycler.

10. The PD system of claim 1, wherein the disposable set being arranged to allow fresh and used dialysis fluid to flow through the micropump head in a same direction includes disposing both the patient line and a drain line of the disposable set, at least during a patient fill phase, downstream of the micropump head.

11. The PD system of claim 1, wherein the first valve actuator is located between the inline fluid heating pathway or the batch heater container and the Y- or T-connector.

* * * * *